United States Patent
Egle et al.

[11] Patent Number: 5,914,401
[45] Date of Patent: Jun. 22, 1999

[54] METHODS FOR THE MANUFACTURE OF QUINOLONE CARBOXYLIC ACIDS DERIVATIVES AND INTERMEDIATES THEREOF

[75] Inventors: Ian Egle; Regis C.S.H. Leung-Toung, both of Mississauga; Bo Lei, Thornhill; Tim Fat Tam, Woodbridge; Tao Xin, North York; Khashayar Karimian, Mississauga, all of Canada

[73] Assignee: Apotex, Inc., Weston, Canada

[21] Appl. No.: 09/037,982

[22] Filed: Mar. 11, 1998

[30] Foreign Application Priority Data

Mar. 11, 1997 [CA] Canada ................................. 2199645

[51] Int. Cl.⁶ ............... C07D 401/00; C07D 265/34; C07D 215/16
[52] U.S. Cl. .................. 544/363; 544/100; 546/153
[58] Field of Search ................... 544/363, 100; 546/153

[56] References Cited

PUBLICATIONS

Chemical Abstracts 121:57343, Kimura, 1993.
Chemical Abstracts 119:271202, Marquillas, 1993.
Chemical Abstracts 119:95358, Murabayashi, 1993.
Chemical Abstracts 117:234043, Marquillas, 1992.
Chemical Abstracts 114:185560, Monserrat, 1989.
Chemical Abstracts 108:167325, Warner–Lambert, 1987.
Chemical Abstracts 106:33116, Gallardo, 1985.
Chemical Abstracts 106:32867, Calatayud, 1985.
Chemical Abstracts, 105:60542, Grohe, 1986.
Chemical abstracts 119:28140, Afonso, 1992.
Chemical Abstracts 112:118668, Schriewer, 1989.
Chemical Abstracts 112:98406, Schriewer, 1989.
Liebenow and Liedtke, "Notz uber eine neue Methode zur Darstellung von 1.3–Dimethy–uracil–carbonsaure–(5)", Chem. Ber. 105:2095–2097 (1972).
Koga et al, "Structure–Activity Relationships of Antibacterial 6,7–and 7,8–Disubstituted 1–Alkyl–1,4–dihydro–4–oxoquinoline–3–carboxylic Acids", J. Med. Chem. 23:1358–1363 (1980).
Bouzard, Daniel, "Recent Advances in the Chemistry of Quinolones", Recent Progress in the Chemical Synthesis of Antibiotics, Springer–Verlag (1990), pp. 250–283.

*Primary Examiner*—D. Margaret M. Mach
*Attorney, Agent, or Firm*—Nixon & Vanderhye P.C.

[57] ABSTRACT

Novel process for the preparation of quinolone carboxylic acid derivatives of general formula I, and intermediates thereof as illustrated in Scheme 1 wherein the key intermediate is a compound of formula IX.

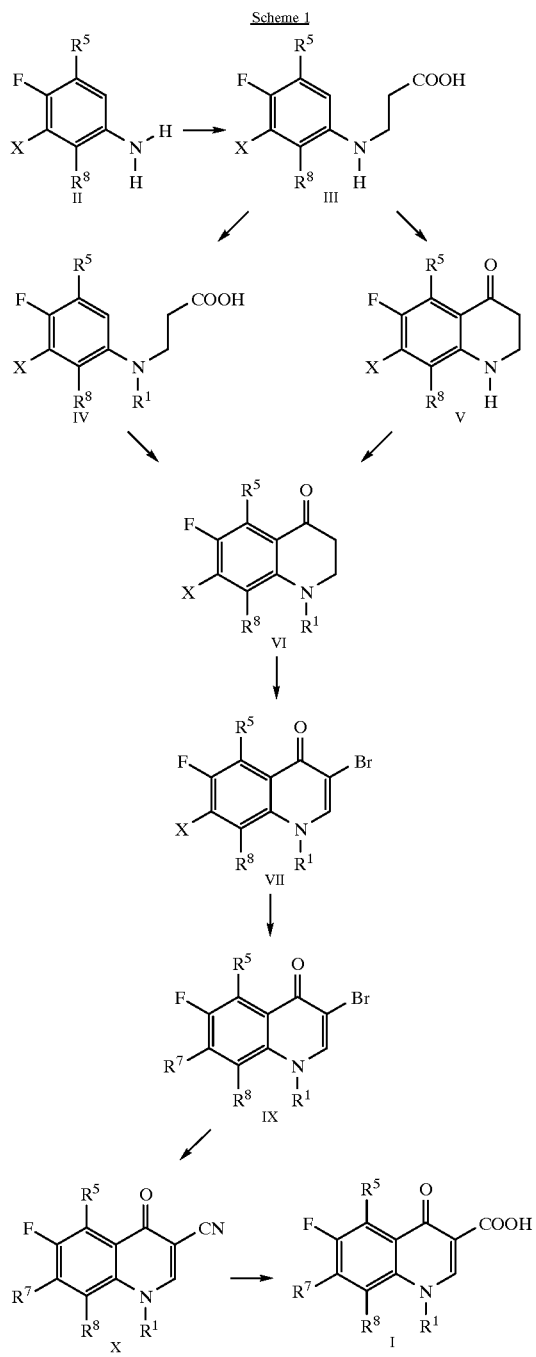

16 Claims, No Drawings

METHODS FOR THE MANUFACTURE OF QUINOLONE CARBOXYLIC ACIDS DERIVATIVES AND INTERMEDIATES THEREOF

FIELD OF THE INVENTION

This invention relates to a novel process for the manufacture of quinolone carboxylic acids of general formula I, wherein

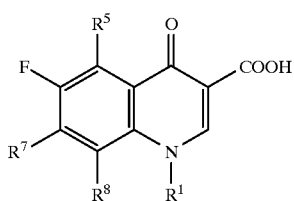

Formula I wherein $R^1$ is $C_1$–$C_8$ alkyl or cycloalkyl;

$R^8$ is hydrogen, $C_1$–$C_8$ alkyl, $C_1$–$C_8$ alkoxy or halogen; or $R^8$ and $R^1$ taken together represent an ether group radical of the formula

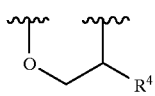

wherein $R^4$ is $C_1$–$C_8$ alkyl.

$R^5$ is hydrogen.

$R^7$ is NRR' wherein R and R' are independently hydrogen, $C_1$–$C_8$ alkyl, pyrrolidinyl, piperazinyl, prolyl, morpholinyl, piperidinyl; or is a group of formula:

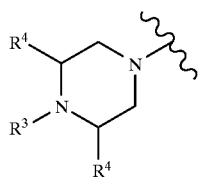

wherein $R^4$ is described as above;

$R^3$ is hydrogen, alkyl, alkoxycarbonyl, carbobenzyloxy carbonyl, alkanolyl; or is a group of formula:

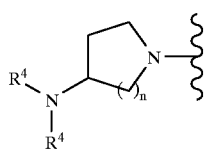

wherein $R^4$ is as described above n is 1 or 2

In a further aspect, the invention also relates to novel intermediates useful in the manufacture of the quinolone carboxylic acid derivatives of formula I and to process for the manufacture of these intermediates.

A preferred embodiment of this invention relates to a method of introducing $R^7$.

In another embodiment, the invention relates to the use of novel bromo derivatives as a precursor in the synthesis of compounds of formula I.

In a further embodiment, this invention deals with the introduction of the CN group as the ultimate precursor in the synthesis of compounds of Formula I.

BACKGROUND OF THE INVENTION

The chemistry of quinolones has been reviewed by D. Bouzard in "Recent Advances in the Chemistry of Quinolones" in Recent Progress in the Chemical Synthesis of Antibiotics by Federico Arcamone, Springer-Verlag, 1990, p. 249–283. Articles by Peterson L. P., Quinolone Resistance in Clinical Practice: Occurrence and Importance, In Quinolone Antimicrobial Agents, 2nd edition; and by Moellering, R. C., Jr. Quinolones Antimicrobial Agents: Overview and Conclusion. American Society for Microbiology: Washington, D.C., 1993 pp 527–535 have been published emphasising the antibacterial and pharmacological properties of quinolones.

Norfloxacin, 1-ethyl-6-fluoro-1,4-dihydro-4-oxo-7-(1-piperazinyl)-3 quinolinecarboxylic acid, is a fluorinated quinolone antibacterial agent and it's pharmacokinetics and antibacterial properties have been reported by B. Holmes et. al., Drugs, 30, 482–513 (1985); R. C. Rowen et. al., Pharmacotherapy 7, 92–110 (1987).

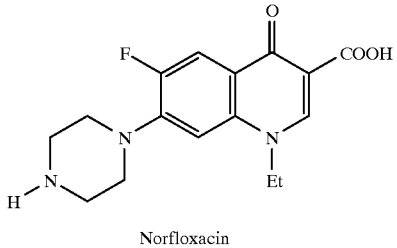

Norfloxacin

Ciprofloxacin, 1-cyclopropyl-6-fluoro-1,4-dihydro-4-oxo-7-(1-piperazinyl)-3-quinolinecarboxylic acid, is an analogue of norfloxacin. The antibacterial activity, pharmacokinetics, and clinical efficacy and safety are reviewed in Chemotherapy (Tokyo), 33, Suppl. 7, 1–1024 (1985) and in Symposium on antibacterial spectrum and clinical use: Am. J. Med. 82, Suppl., 4A, 1–404 (1987).

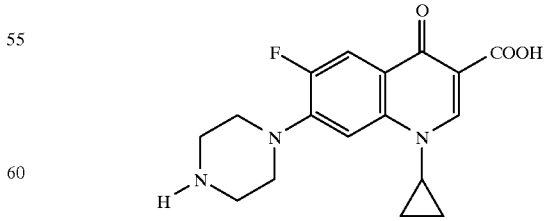

Ciprofloxacin

Ofloxacin, (2) (±)-9-fluoro-2,3-drhydro-3-methyl-10-(4-methyl-1-piperazinyl)-7-oxo-7H-pyrido[1,2,3-de]-1,4- benzoxazine-6-carboxylic acid, is another analogue of norfloxacin. The medicinal chemistry of ofloxacin is reported in Imamaura et. al., Antimicrob. Agents Chemother. 1987, 31, 325 and in Daichi, S. Drugs Future, 1983, 8, 395.

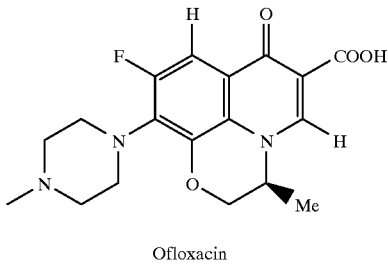

Ofloxacin

Lomefloxacin, 1-ethyl-6,8-difluoro-1,4-dihydro-4-oxo-7-(3-methyl-1-piperazinyl)-3-quinolinecarboxylic acid, is another close analogue of norfloxacin. Its preparation has been reported in U.S. Pat. No. 4,528,287 and the biological properties of the compound are reported by T. Hirose et. al., in Antimicrob. Ag. Chem.ther. 31, 854, 1987.

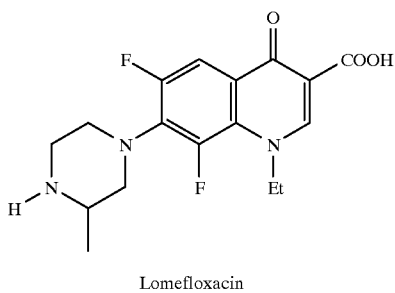

Lomefloxacin

Norfloxacin, Ciprofloxacin, Ofloxacin, Lomefloxacin are approved oral antibacterials.

PRIOR ART

The synthesis of norfloxacin is described in J. Med. Chem., 1980, 23, 4358, Hiroshi, et. al. and is illustrated in Scheme 2:

Scheme 2

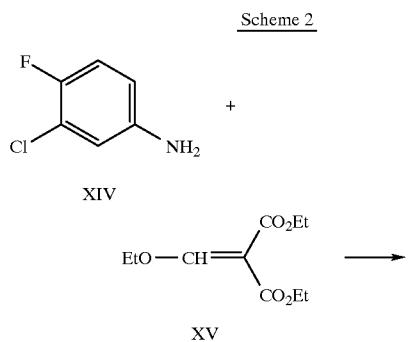

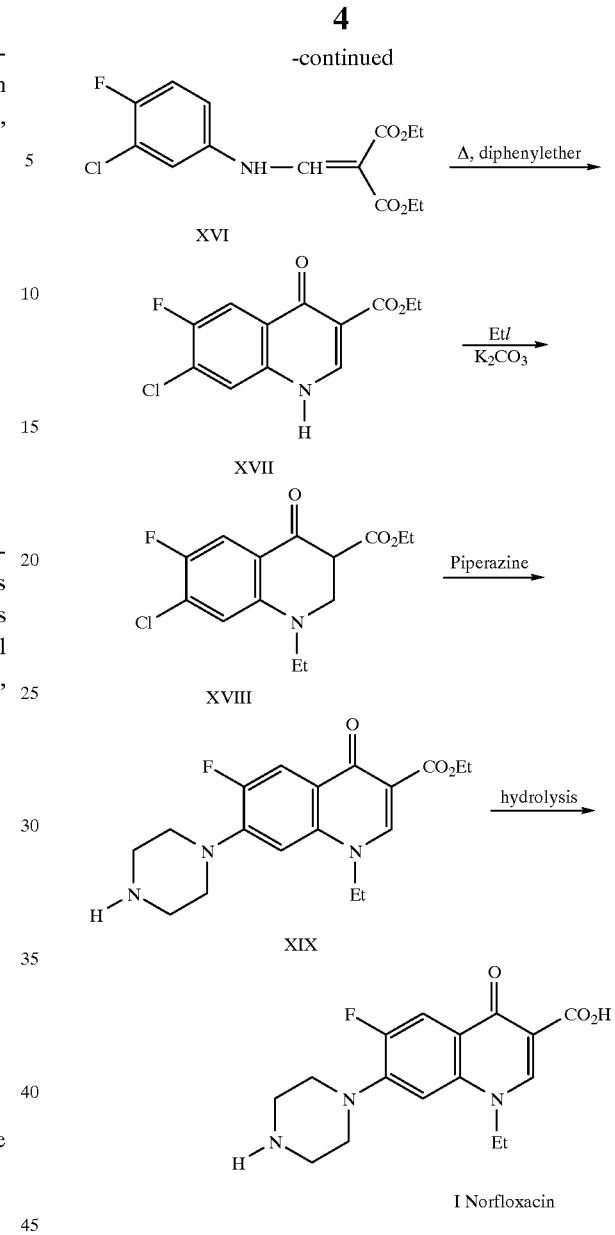

Compound XIV is reacted with diethyl ethoxyethylene malonate XV which is heated in diphenyl ether to give the quinolone XVII. The later compound is alkylated with ethyl iodide in the presence of a base to give compound XVIII. The key step in the Norfloxacin synthesis involves the introduction of a piperazine moiety onto compound XVIII to give compound XIX at high temperature. The acid hydrolysis of the ester XIX affords Norfloxacin I.

Every Canadian process patent pertaining to norfloxacin deals with methods of condensing two components, namely piperazine or a derivative and 1-ethyl-6-fluoro-7-halo-1,4-dihydro-4-oxoquinoline-3-carboxylic acid or a derivative.

In Canadian patent 1,178,961 piperazine is condensed with 1-ethyl-6-fluoro-7-chloro-1,4-dihydro-4-oxo-quinoline-3-carboxylic acid to give norfloxacin. Canadian patent 1,214,466 claims the process of making the ester analogues of norfloxacin by the condensation of piperazine with the ester of the above compound. Hydrolysis of the ester leads to norfloxacin. Canadian patent 1,273,936 relates only to the synthesis of the quinolone carboxylic acid by cyclocondensation of a 2-benzoyl-3-amino-acrylonitrile followed by hydrolysis.

Canadian Patent 1,284,800 relates to intermediates useful in the preparation of norfloxacin which are said to enhance the selectivity of the nucleophilic displacement of chlorine by an amine in position 7. Such intermediates are in the form of boron complex which are prepared by reaction of 1-ethyl-6-fluoro-7-chloro-1,4-dihydro-4-oxo-quinoline-3-carboxylic acid or ester with a boron derivative.

Canadian Patent 1,325,010 relates to a process for the preparation of quinoline carboxylic acid derivatives which consists in reacting the boron derivative disclosed in Canadian Patent 1,284,800 with piperazine followed by hydrolysis.

Canadian Patent 1,312,603 discloses a process to prepare quinoline-carboxylic acid derivatives and amongst them norfloxacin by reaction of 1-ethyl-6-fluoro-7-chloro-1,4-dihydro-4-oxo-quinoline-3 carboxylic acid ester and/or acid with a N-formylated piperazine and dimethylformamide to form a piperazine derivative which is then hydroylzed to give norfloxacin.

Canadian Patent 1,326,239 issued recently describes a process for preparing quinoline carboxylic acid derivatives and amongst them norfloxacin by reaction of 1-ethyl-6-fluoro-7-chloro-1,4-dihydro-4-oxo-quinoline carboxylic acid with an N-alkoxycarbonyl substituted piperazine followed by hydrolysis.

The prior art discloses three methods to perform the condensation reaction. As shown in Scheme 2 in all three methods norfloxacin is prepared from the key intermediate XVIII or the carboxylic acid analogue.

The three patented procedures have the following shortcomings:
1. The cyclization of XVI to quinolone derivative XVII requires high reaction temperature in the range of 250° C.
2. An ether (diphenyl ether) is used as a solvent which is an expensive solvent.
3. The reaction between piperazine or a piperazine derivative and the ethyl ester XVIII requires the use of refluxing pyridine. Pyridine is a very toxic solvent. An improvement in Canadian Patent 1,325,010 is the use of boric acid ester which is reacted with piperazine to prepare the boric acid anhydride of norfloxacin. However, the removal of the boric acid impurity is a problem in large scale manufacturing.

In the case of ciprofloxacin, the synthesis of the quinolonecarboxylic acid is claimed in Canadian patents 1,218,067, 1,237,431, 1,273,936, 1,283,112, and 1,283,658. Canadian patent 1,273,936 describes the synthesis of the 3-nitrile analogue of the quinolonecarboxylic acid. It does not describe its condensation with amines.

The condensation of the quinolonecarboxylic acid with various disubstituted amines, including piperazine and its derivatives, is claimed in Canadian patents 1,218,067, 1,246,574, 1,326,239, and 1,290,339.

Canadian Patent 1,218,067 describes the synthesis of ciprofloxacin by a multi-step process as illustrated in Scheme 3. Compound XXX is prepared in seven steps from compound XXIII. The ketoester XXX is reacted with triethyl orthoformate to give compound XXXI which is reacted with cyclopropylamine to give XXXII. The later compound cyclizes to give quinolone XXXIII. Introduction of piperazine affords XXXIV which is then hydrolyzed to ciprofloxacin. This is a twelve step synthesis from commerically available materials.

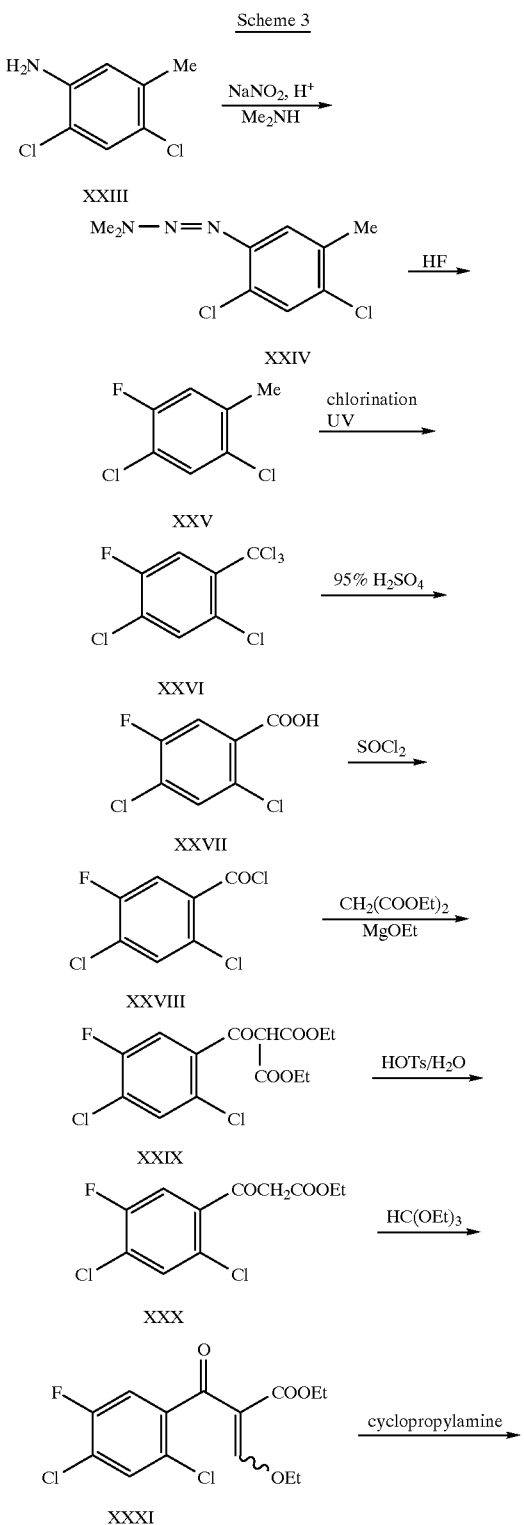

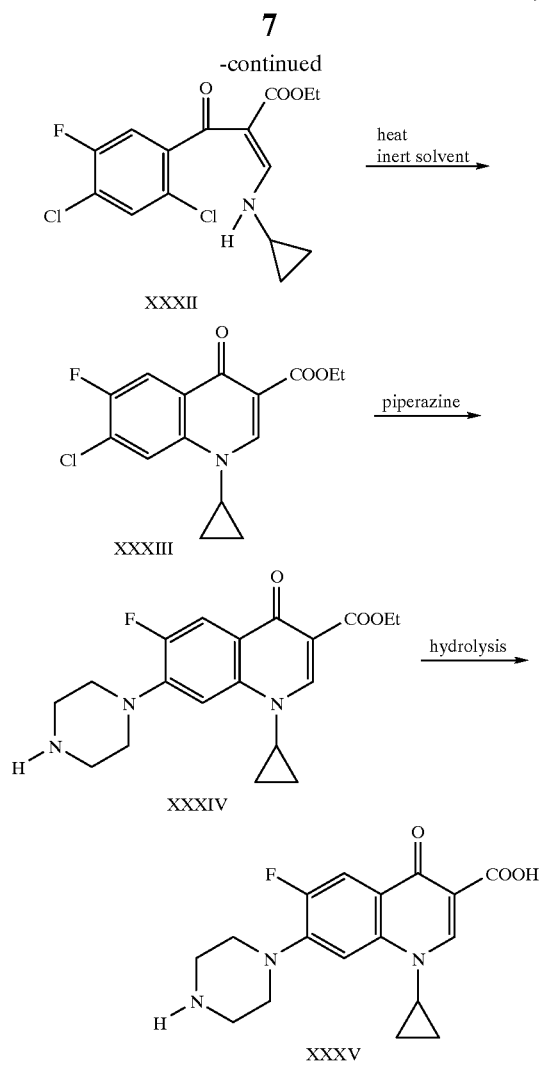

XXXII

XXXIII

XXXIV

XXXV

Canadian Patent 1,246,574 describes similar procedures for the preparation of ciprofloxacin and derivatives as outlined in Scheme 4. The later patent provides a procedure for the preparation of ciprofloxacin from carboxylic acid XXXXI which is the acid derivative of compound XXXIII (Scheme 3) in Canadian patent 1,218,067.

Canadian Patent 1,273,936 reports a procedure for the preparation of the starting material XXXXI described in Canadian patent 1,246,574.

The piperazine moiety is then introduced to the ester XXXIII (Scheme 3) or the acid XXXXI (Scheme 4) to give ciprofloxacin ethyl ester and ciprofloxacin. Scheme 5 highlights the key reactions in the approaches used in Schemes 3 and 4. In all these procedures the starting material ester XXX (Scheme 3) and nitrile XXXVII (Scheme 4) are prepared by a multi-step synthesis, using expensive starting material.

Two approaches have been reported for the synthesis of ofloxacin in a number of journal articles such as Tanaka Y. et. al., Chem Pharm. Bull. 1984, 32, 4923; Hayakawa I. et. al., Chem Pharm. Bull. 1984, 32, 4907; and Egawa H. et. al., Chem Pharm. Bull. 1986, 34, 4096. Patented processes also fall within the two reported synthetic methodologies.

Canadian Patent 1,167,840 describes a method for the conversion of 2,3,4-trifluoronitrobenzene to ofloxacin as illustrated in Scheme 6. Alkaline hydrolysis of XXXXII in DMSO occurred selectively at the halogen atom adjacent to the nitro group to yield the phenol XXXXIII which was alkylated to XXXXIV. Reductive cyclization of XXXXIV followed by condensation with diethylethoxymethylene malonate and heating in polyphosphoric acid at 145° C. affords the ester XXXXVI. Acid hydrolysis gave the free acid XXXXVII which reacted with N-methyl piperazine to give ofloxacin. The chemical reaction sequences involved in the conversion of amine XXXXV to Ofloxacin (Scheme 8) is similar to those used in the preparation of norfloxacin from amine XIV (Scheme 2). Canadian patent 1,167,840 claims only the condensation of the quinolonecarboxylic acid XXXXVII (Scheme 6) or its ester analogue with an amine (i.e. 4-methylpiperazine for ofloxacin).

Scheme 4

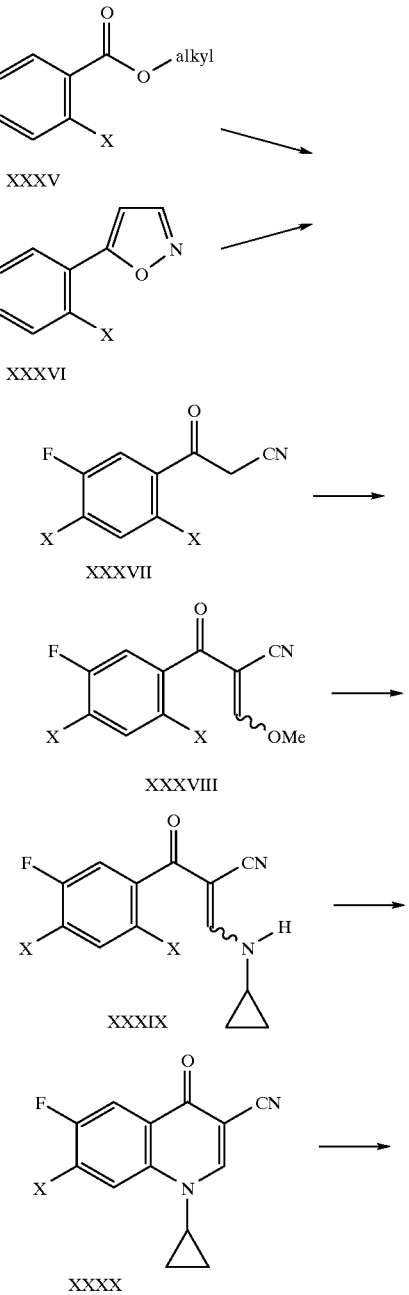

XXXV

XXXVI

XXXVII

XXXVIII

XXXIX

XXXX

-continued
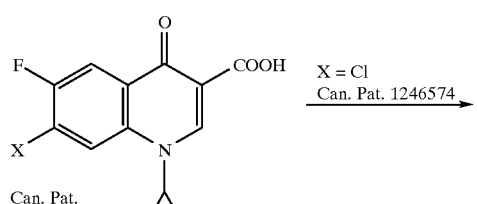
XXXXI
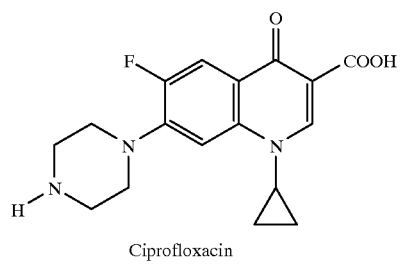
Ciprofloxacin
-continued
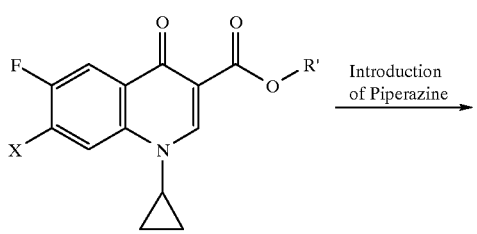
R' = BR₂, H, Et
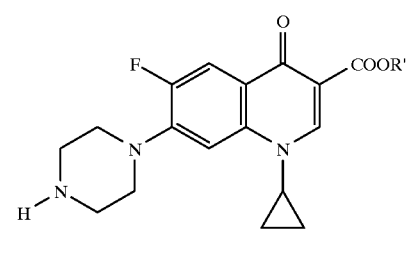
R' = H, Ciprofloxacin
Scheme 5
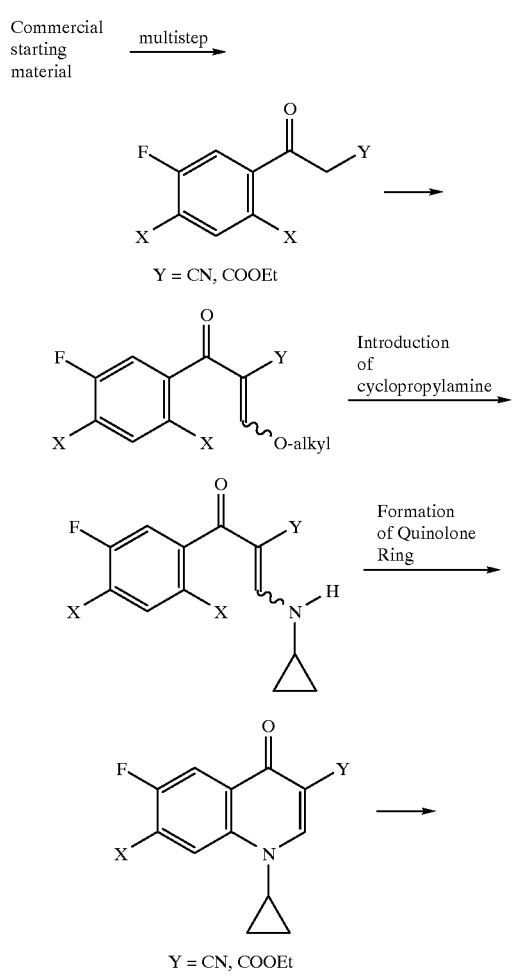
Scheme 6
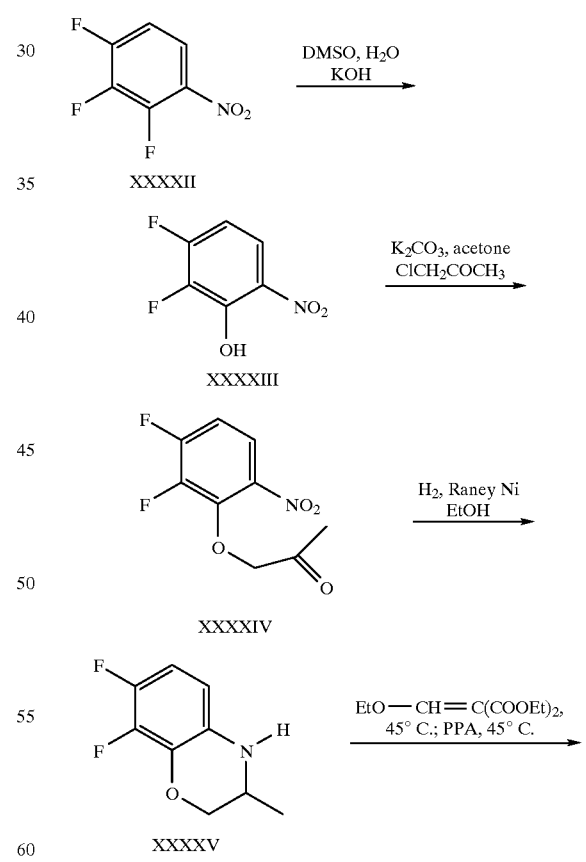

11
-continued
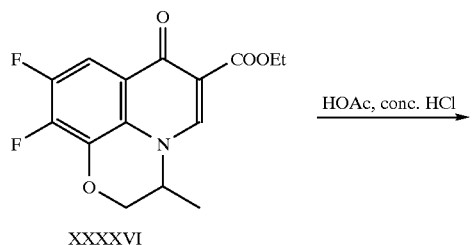
XXXXVI
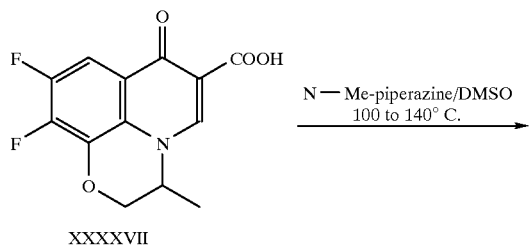
XXXXVII
12
-continued
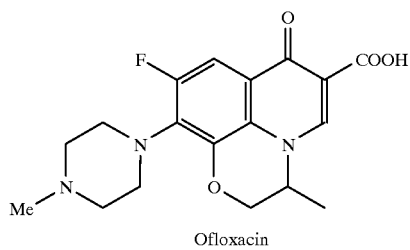
Ofloxacin
The second method of production of ofloxacin starts from the tetrafluoro intermediate XXXXVIII as described in Scheme 7.
Scheme 7
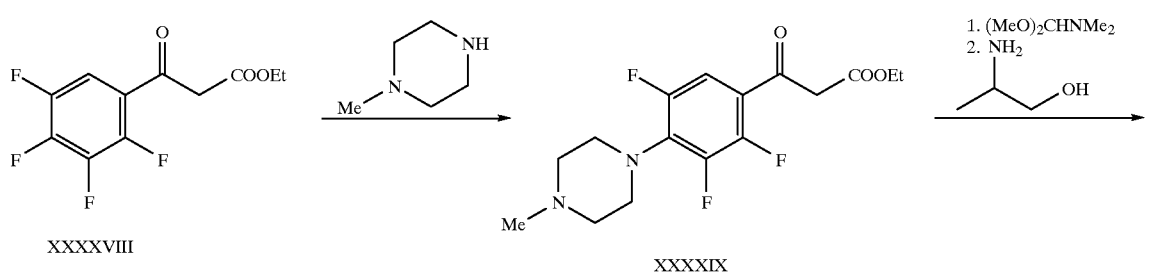
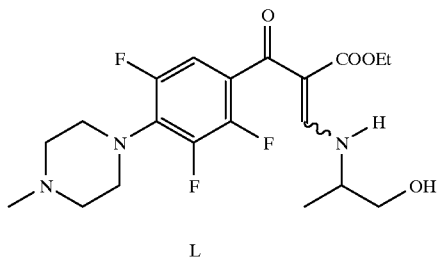
L

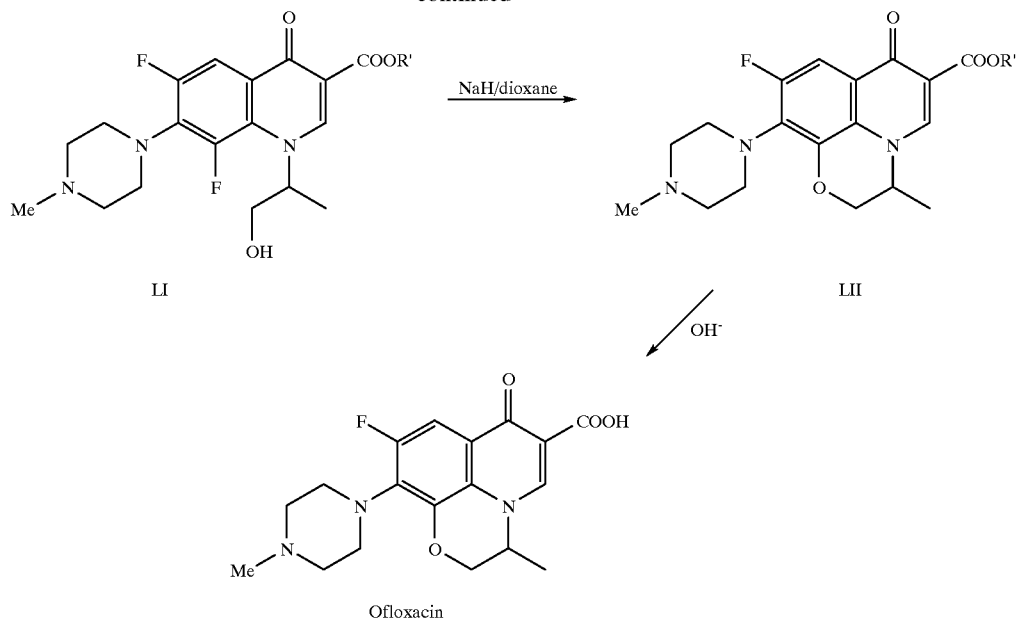

N-methylpiperazine was first introduced into compound XXXXVIII which was converted to enaminoketoester L on treatment with N,N-dimethylformamide dimethyl acetal in toluene followed by the reaction with 2-amino-1-propanol in ethanol. Reaction of enaminoketoester L with potassium fluoride in DMF gave quinoline LI which was cyclized with strong base such as sodium hydride to give the ester LII. Alternatively, enaminoketoester L may be reacted with sodium hydride in dioxane to yield the ester LII which was hydrolyzed with sodium hydroxide to give Ofloxacin.

The second method uses as starting material, 2,3,4,5-tetrafluorobenzoic acid which is an expensive compound. The quinoline ring formation steps (XXXXIX to LII) shown in scheme 7 are very similar to the steps used in the synthesis of ciprofloxacin (Scheme 3, XXX to XXXIII). The major difference is that in the ofloxacin synthesis the piperazine ring (XXXXVIII to XXXXIX) is introduced at a very early stage of the synthesis.

In summary, there are two general methods for the preparation of quinolones. Norfloxacin, ciprofloxacin and ofloxacin all have a piperazine ring or derivative thereof at the 7-position of the quinolone. The first general approach involves:

(a) closing the ring at the 4-position with appropriate olefinic precursor (e.g. XVI to XVII, Scheme 2; XXXXV to XXXXVI, Scheme 6); followed by (b) introduction of the piperazine ring at the end of the synthesis. Among the processes involved, there appears that the presence of a carboxylic acid, its ester or a boron complex thereof is a prerequisite for activation of C-7 towards nucleophilic displacement of chlorine by a piperazine. This is, in fact, explicitly stated in a review article by Bouzard in "Recent Progress in the Chemical Synthesis of Antibiotics" "Recent Advances in the Chemistry of Quinolones" by Federico Arcamone, Springer-Verlag, 1990, p. 249–283.

The second general approach involves:

(a) The preparation of the enaminoketoesters and then cyclizing them to give the quinolone ring.

(b) Depending on the target molecules, the piperazine moiety is introduced at the C-7 position at the last stage of the synthesis (e.g. ciprofloxacin, Scheme 3 and 4) or at a very early stage in the synthesis, Scheme 7).

The prior art teaches that the nucleophilic substitution of a chlorine by a piperazine works well with a strongly electron withdrawing group at position 3. Examples of strong electron withdrawing group reported in the literature include carboxylic acid ester, boron complex and carboxylic acid group. The reaction with the later group requires vigorous conditions and proceeds in modest yields with considerable formation of by products. This is caused by the partial ionization of the carboxylic acid group which reduces its electron withdrawing effect.

Accordingly, any nucleophilic substitution carried out in the presence of a weakly electron withdrawing at position 3 such as a bromine would not be expected to work. In the present invention it was surprisingly found that the nucleophilic substitution of the 7-halo atom by a protected piperazine could be obtained when the substituent in position 3 was a weakly electron withdrawing group such as bromine and that such reaction could be carried out in high yield. Furthermore, such reaction avoids the presence of undesirable side product observed in by the prior art. As a further advantage, the process of our invention does not require the use of diphenyl ether or a boric acid derivative for the introduction of the piperazine ring at the 7 position of the quinolone which are not recommended in large scale manufacturing.

Our general synthesis of quinolone carboxylic acids is applicable to norfloxacin and analogues such as ciprofloxacin, lomefloxacin and ofloxacin. Therefore, one object of the present invention is to provide a novel process for the production of quinolone carboxylic acids from inexpensive and relatively safe starting material. Other objects of this invention can be recognized by those skill in the art from the summary of invention and detailed description of embodiments thereof.

SUMMARY OF INVENTION

The present invention provides a process for the manufacture of compounds of formula I:

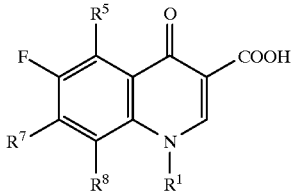

Formula I wherein $R^1$ is $C_1$–$C_8$ alkyl or cycloalkyl;

$R^8$ is hydrogen, $C_1$–$C_8$ alkyl, $C_1$–$C_8$ alkoxy or halogen; or $R^8$ and $R^1$ taken together represent an ether group of the formula

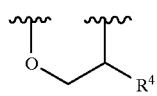

wherein $R^4$ is hydrogen or $C_1$–$C_8$ alkyl.

$R^5$ is hydrogen.

$R^7$ is NRR' wherein R and R' are independently hydrogen, $C_1$–$C_8$ alkyl, pyrrolidinyl, piperazinyl, prolyl, morpholinyl, piperidinyl; or is a group of formula:

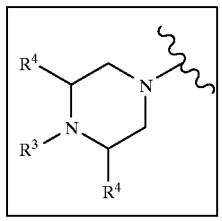

wherein $R^4$ is described as above;

$R^3$ is hydrogen, alkyl, alkoxycarbonyl, carbobenzyloxy carbonyl, alkanolyl; or is a group of formula:

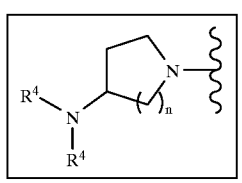

wherein $R^4$ is as described above; n is 1 or 2 which comprises the following steps:

(a) brominating a compound of formula VI:

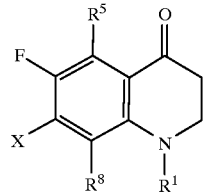

Formula VI wherein $R^1$, $R^5$ and $R^8$ are as described above

X is halogen to give a compound of formula VII

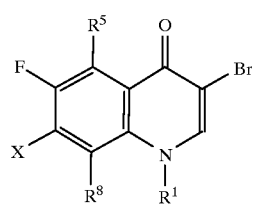

Formula VII wherein $R^1$, $R^5$, $R^8$ and X are described above;

(b) reacting a compound of formula VII with an amine of formula $R^7H$, to give a compound of formula IX

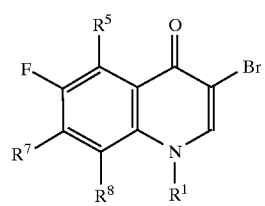

Formula IX wherein $R^1$, $R^5$, $R^7$ and $R^8$ are as described above;

(c) reacting a compound of formula IX to give a compound of formula X

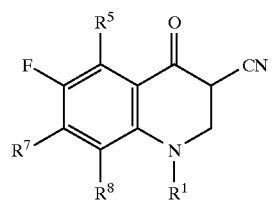

Formula X wherein $R^1$, $R^5$, $R^7$ and $R^8$ are as described above; followed by:

(d) hydrolysing the compound formula X to give a compound of formula I.

DETAILED DESCRIPTION OF THE INVENTION

Scheme 1 illustrates the novel process of this invention. In the formulas, $R^1$ represents $C_1$–$C_8$ alkyl or cycloalkyl, $R^8$ represents hydrogen, $C_1$–$C_8$ alkyl, $C_1$–$C_8$ alkoxy or halogen or $R^8$ and $R^1$ taken together represent an ether group of the formula:

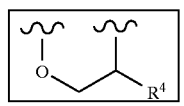

wherein $R^4$ is hydrogen or $C_1$–$C_8$ alkyl, $R^7$ represents NRR' wherein R and R' are independently hydrogen or $C_1$–$C_8$ alkyl, pyrrolidinyl, piperazinyl, prolyl, morpholinyl, piperidinyl, or a group of the formula:

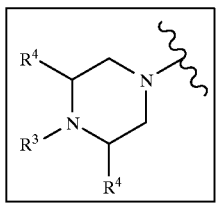

wherein $R^3$ represents hydrogen, alkyl, alkoxycarbonyl, carbobenzyloxycarbonyl, alkanoyl; or a group of formula:

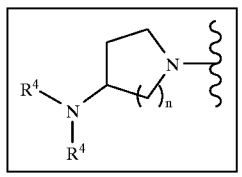

wherein n is 1 or 2.

As used herein the term "$C_1$–$C_8$ alkyl" refers to the straight or branched chain lower alkyl hydrocarbon groups having one to 8 carbon atoms such as methyl, ethyl, n-propyl, iso-propyl, n-butyl, sec-butyl, iso-butyl, t-butyl, n-pentyl and like alkyl groups; the term "cycloalkyl" refers to a $C_3$–$C_8$ cyclic alkane the term halogen refers to fluoro, chloro, bromo and iodo and preferably fluoro or chloro the term alkoxycarbonyl refer to a group of formula:

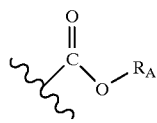

wherein $R_A$ is an alkyl group as defined above
the term alkanoyl refers to a group of formula:

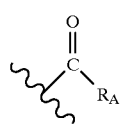

wherein RA is an alkyl
the term carbobenyzloxylcarbonyl refers to a group of formula:

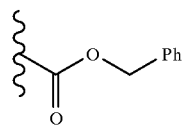

Bromination of compound VI in acetic acid yields the 3-bromoquinolone derivative VII. The bromination is carried out using 0.5 moles of VI in 300 ml glacial acetiz acid and 1.05 moles bromine at 35–80° C., and preferably between 50–60° C. to afford 95° yield of the bromination product after usual work up.

Compound VII is then reacted with a piperazine and preferably ethoxycarbonylpiperazine. The amination is carried out using the amine as reaction solvent at a temperature between 110° C.–130° C. and preferably 110–115° C. to produce compound IX. Compound IX is then converted to a nitrile derivative of formula X. The reaction takes place in the presence of KCN, CuI and in a high boiling dialkylamide and preferably 1-methyl-2-pyrrolidinone at a temperature between 190° C. and 210° C. Hydrolysis of compound X in the presence of a base leads to compound of formula I. The hydrolysis takes place in aqueous alcohol and preferably aqueous ethanol and base, preferably sodium hydroxide at 110° C.

Compound VI is prepared by intramolecular Friedel-Crafts acylation of compound IV in the presence of a catalyst such as the Eaton's reagent at a temperature between 110° C. and 130° C. Compound IV is the product obtained after N-alkylation of compound III. The N-alkylation is carried out with an alkylating agent such as alkyl iodide or dialkylsulfate, and preferably in the presence of a strong base such as metal hydroxides and preferably sodium hydroxide. Compound III is obtained by conventional manner well known in the art.

In a further embodiment, the invention further produces a process to make the new intermediate of formula VII. In yet a further embodiment, the invention provides a process to make another precursor of compound of formula I, the compound of formula IX.

In a preferred embodiment, ciprofloxacin and norfloxacin are prepared by the process of the present invention. In a further embodiment ofloxacin and lomefloxacin are also prepared according to the process of the present invention.

The present invention will be more fully understood by the following examples which illustrate the invention, but are not considered limiting to the scope of the invention.

EXPERIMENTAL

Example 1

3-(3',4'-Difluorophenylamino)propionic acid (formula III)

3,4-Difuoroaniline (204 g, 1.58 mol) was dissolved in a mixture solvent of toluene (300 ml) and heptane (150 ml) and acrylic acid (114 g, 1.58 mol) was added. The solution was stirred at 40° C. for 14 hours, then heated to 80° C. and stirred for 1.5 hour. The solution was allowed to cool to room temperature 400 ml of heptane was added, and the suspension was stirred for 1 hour with ice-bath cooling. The solids were collected by filtration, washed with heptane, and dried to give 250 g of 3-(3',4'-Difluorophenylamino) propionic acid III (79% yield).

$^1$H nmr (CDCl$_3$) δ 7.37 (br, 2H, NH$_2$$^+$), 6.98 (dd, 1H, J=8.9 Hz, phenyl H), 6.43 (dq, 1H, J=2.79, 6.57, 12.5 Hz, phenyl H), 6.28–6.33 (m, 1H, phenyl H), 3.41 (t, 2H, J=6.2 Hz, CH$_2$), 2.68 (t, 2H, J=6.3 Hz, CH$_2$).

$^{13}$C nmr (CDCl$_3$) d 178.3, 151.2 (J$_{CF}$=13.4, 245 Hz), 145.3, 143.7 (J$_{CF}$=8.8, 188 Hz), 117.8 (J$_{CF}$=18 Hz), 108.6, 102.1 (J$_{CF}$=20.8 Hz), 39.9, 33.7.

MP: 82–86° C.

IR (KBr) cm$^{-1}$: 1692 (C=O).

HRMS (m/e: C$_9$H$_9$F$_2$NO$_2$) calc. 201.0601, found 201.0605.

Example 2

3-[N-(3',4'-Difuorophenyl)-N-ethyl]propionic acid (formula IV)

Method A

Compound from example 1 (20 g, 0.1 mol) was dissolved in 25% NaOH (40 ml) and diethyl sulfate (23 g, 0.15 mol) was added. The solution was stirred at room temperature for 14 hours and then heated to 70° C. for 2 hours to destroy diethyl sulfate. The reaction mixture was acidified with 6N HCl (with ice-bath cooling) to pH 4 and extracted with CH$_2$Cl$_2$ (50 ml×2). The combined extract was washed with brine, dried over Na$_2$SO$_4$, and concentrated to give 22 g crude product 3-[N-(3',4'-Difuorophenyl)-N'-ethylamino] propionic acid as a brown oil (96% yield based on crude product), which was used directly for the consequent reaction.

Method B

Compound from example 1 (83 g, 0.41 mol) was dissolved in a mixture solution of 2-propanol (250 ml) and 50% NaOH (120 ml). The mixture was heated to 60° C. and stirred for 1 hour. Iodoethane (170 g, 1.09 mol) was added and the mixture was heated to gentle refluxing for 14 hours. The resulting mixture was concentrated to remove most solvents and he residue was dissolved in 200 ml water. The solution was acidified with 6N HCl to pH 3, extracted with EtOAc (400ml×3). The combined EtOAc solution was washed with brine, dried over Na$_2$SO$_4$, and concentrated to give 93 g crude product as brown oil (98% yield based on crude product), which was used directly for the consequent reaction.

A small amount of crude product was purified by column chromatography (1% MeOH/CH$_2$Cl$_2$) to give IV as a light yellow oil.

$^1$H nmr(CDCl$_3$): δ 11.44 (br s, 1H, OH), 7.01 (dd, 1H, J=9.3 Hz, phenyl H), 6.52 (dq,1H, J=3.0, 6.6, 13.8 Hz, phenyl H), 6.36–6.41 (m, 1H, phenyl H). 3.58 (t, 2H, J=7.3 Hz, CH$_2$), 3.33 (q, 2H, J=7.1 Hz, CH$_2$), 2.63 (t, 2H, J=6.3 Hz, CH$_2$), 1.14 (t, 3H, J=7.1 Hz).

$^{13}$C nmr (CDCl$_3$) δ 178.3, 151.2 (J$_{CF}$=13, 245 Hz), 144.6, 143.1 (J$_{CF}$=1.3, 244 Hz), 117.8 (J$_{CF}$=18 Hz), 108.5, 102.3 (J$_{CF}$=20.8 Hz), 46.0, 46.6, 32.5, 12.1.

IR (neat) cm$^{-1}$: 1629 (C=O).

HRMS (m/e: C$_{11}$H$_{13}$F$_2$NO$_2$) calc. 229.0914, found 229.0931.

Example 3

1-Ethyl-6,7-difluoro-1,2,3,4-tetrahydro-4-oxo-quinoline and 1-Ethyl-5,6-difluoro-1,2,3,4-tetrahydro-4-oxo-quinoline (formula VI)

Preparation of Eaton's reagent

With vigorous stirring, P$_2$O$_5$ (10% w/w) was added in one portion to methansulfonic acid at room temperature and the mixture was stirred for 2 hr. The resulting solution was quickly filtered to remove insoluble solids. The reagent was kept at room temperature and protected from moisture.

Compound from example 2 (60 g, 0.26 mol) was mixed with Eaton's reagent (600 g) and the mixture was heated to 100–110° C. The mixture was stirred at that temperature for 2.5 hr to complete the reaction. The mixture was cooled to 50° C., poured to 500 ml cold water, and extracted with CH$_2$Cl$_2$ (200 ml×3). The combined CH$_2$Cl$_2$ solution was washed with sat. NaHCO$_3$ and brine, dried over Na$_2$SO$_4$, and concentrated to give 41.5 g (yield 75%) of product as yellow solids, which was a 2:1 mixture of the isomers VI.

A small amount of the mixture product was purified by column chromatography (1% MeOH/CH$_2$Cl$_2$) to give 1-ethyl-6,7-difluoro-1,2,3,4-tetrahydro-4-oxo-quinoline and 1-ethyl-5,6-difluoro-1,2,3,4-tetrahydro-4-oxo-quinoline respectively.

1-Ethyl-6,7-difluoro-1,2,3,4-tetrahydro-4-oxo-quinoline $^1$H nmr (CDCl$_3$): δ 7.64 (dd, 1H, J=9.5, 10.3 Hz, phenyl H), 6.47 (dd,1H, J=6.4, 13.1 Hz, phenyl H), 3.48 (t, 2H, J=7.2 Hz, CH$_2$), 3.39 (q, 2H, J=7.1 Hz, CH$_2$), 2.66 (t, 2H, J=7.2 Hz, CH$_2$), 1.17 (t, 3H, J=7.1 Hz).

$^{13}$C nmr (CDCl$_3$): δ 191.6, 155.9 (J$_{CF}$=14, 253 Hz), 149.1 (J$_{CF}$=10 Hz), 143.1 (J$_{CF}$=14, 239 Hz), 116.2 (J$_{CF}$=3, 17 Hz), 115.8, 108.5, 101.5 (J$_{CF}$=22 Hz), 48.5, 46.2, 37.8, 10.7.

MP: 74–82° C.

IR (KBr) cm$^{-1}$: 1671 (C=O).

HRMS (m/e: C$_{11}$H$_{11}$F$_2$NO) calc. 211.0809, found 211.0827.

1-Ethyl-5,6-difluoro-1,2,3,4-tetrahydro-4-oxo-quinoline respectively $^1$H nmr (CDCl$_3$): δ 7.17 (dd, 1H, J=9.5, 18 Hz, phenyl H), 6.47 (ddd, 1H, J=2.1, 3.2, 9.5 Hz, phenyl H), 3.40–3.50 (m, 4H, 2CH$_2$), 2.68 (t, 2H, J=7.2 Hz, CH$_2$), 1.17 (t, 3H, J=7.1 Hz).

$^{13}$C nmr (CDCl$_3$) δ 191.5, 150.4 (J$_{CF}$=13, 263 Hz), 148.3, 142.3 (J$_{CF}$=13, 237 Hz), 123.4 (J$_{CF}$=15.6 Hz), 110.2, 107.8, 48.3, 46.4, 39.2, 10.8.

MP: 65–66° C.

IR (KBr) cm$^{-1}$ 1673 (C=O).

HRMS (m/e: C$_{11}$H$_{11}$F$_2$NO) calc. 211.0809, found 211.0825.

Example 4

1-Ethyl-3-bromo-6,7-difluoro-1,4-dihydro-4-oxo-quinoline and 1-Ethyl-3-bromo-5,6-difluoro-1,4-dihydro-4-oxo-quinoline (formula VII)

The 2:1 mixture of product from example 3 (105 g, 0.5 mol) was dissolved in acetic acid (300 ml) and bromine (168 g, 1.05 mol) was added dropwise over period of 50 min. The reaction was exothermic and the internal temperature was maintained between 50–60° C. After the addition was completed the reaction mixture was stirred for further 30 min and then carefully poured into 1.5 L ice-water under a vigorous stirring. The suspension was stirred at room temperature for 1 hr and filtered to give crude product as yellow solids. The solid was collected by filtration, washed with 2 L cold water and dried to give 136 g (yield 95%) of product as a 2:1 mixture of 1-ethyl-3-bromo-6,7-difluoro-1,4-dihydro-4-oxo-quinoline and 1-ethyl-3-bromo-5,6-difluoro-1,4-dihydro-4-oxo-quinoline. A 4:1 mixture enriched in 1-ethyl-3-bromo-6,7-difluoro-1,4-dihydro-4-oxo-quinoline could be obtained by recrystallization of the 2:1 mixture from ethanol.

1-Ethyl-3-bromo-6,7-difluoro-1,4-dihydro-4-oxo-quinoline was isolated from the mixture by column chromatography (3:7 EtOAc/hexane) to give a light yellow solid.

$^1$H nmr (CDCl$_3$): δ 8.16 (dd,1H, J=8.8, 10.2 Hz, phenyl H), 8.10 (s, 1H, vinyl H), 7.35 (dd, 1H, J=6.3, 11.2 Hz, phenyl H), 4.27 (q, 2H, J=7.3 Hz, NCH$_2$), 1.56 (t, 3H, J=7.3 Hz).

$^{13}$C nmr (CDCl$_3$) δ 172.1, 154.2 (J$_{CF}$=15, 257 Hz), 148.7 (J$_{CF}$=14, 251 Hz), 144.2, 135.9 (J$_{CF}$=9 Hz), 122.4, 114.9 (J$_{CF}$=19 Hz), 104.9, 104.9 (J$_{CF}$=22 Hz), 49.5, 14.5.

MP: 234–236° C.

IR (KBr) cm$^{-1}$: 1637 (C=O).

HRMS (m/e: C$_{11}$H$_8$BrF$_2$NO)calc. 286.9757, found 286.9761.

1-Ethyl-3-bromo-5,6-difluoro-1,4-dihydro-4-oxo-quinoline was purified by preparative TLC (5:65:30 CH$_2$Cl$_2$/EtOAc/hexane) to give a white solid.

$^1$H nmr (CDCl$_3$) δ 7.89 (s, 1H, vinyl H), 7.29 (dd, 1H, J=9.4, 17 Hz, phenyl H), 7.35 (dd, 1H, J=9.4 Hz, phenyl H), 4.00 (q, 2H, J=7.2 Hz, NCH$_2$), 1.23 (t, 3H, J=7.2 Hz).

$^{13}$C nmr (CDCl$_3$) δ 169.9, 148.6 (J$_{CF}$=13, 210 Hz), 145.2 (J$_{CF}$=12, 191 Hz), 142.4, 136.1, 120.8 (J$_{CF}$=20 Hz),, 116.6, 111.3, 105.6, 48.4, 13.8.

IR (KBr) cm$^{-1}$ 1623 (C=O).

MP: 192–199° C.

HRMS (m/e: C$_{11}$H$_8$BrF$_2$NO) calc. 286.9757, found 286.9774.

Example 5

4-(3-Bromo-1-ethyl-6-fluoro-4-oxo-1,4-dihydroquinolin-7-yl)-piperazine-1-carboxylic acid ethyl ester and 4-(3-Bromo-1-ethyl-6-fluoro-4-oxo-1,4-dihydroquinolin-5-yl)-piperazine-1-carboxylic acid ethyl ester (formula IX)

(i) A (4:1) mixture of product from example 4 (23.0 g, 79.9 mmol) in neat ethyl 1-piperazine carboxylate (63.1 g, 0.34 mol) was heated at 120–125° C. for 6 hours. After cooling to room temperature, the reaction mixture was diluted with dichloromethane and the organic layer was washed with sat. NH$_4$Cl solution (2×).

A solid suspension formed and was filtered off. The organic layer was separated and washed with water (3×), dried (Na$_2$SO$_4$), filtered and concentrated in vacuo to give 34.2 g of a brown solid.

The solid was suspended in hot ethyl acetate for 2 h then stirred at room temperature for 16 hours. Filtration gave 24.5 g of 4-(3-bromo-1-ethyl-6-fluoro-4-oxo-1,4-dihydroquinolin-7-yl)-piperazine-1-carboxylic acid ethyl ester as a white solid (95% pure by Rp-HPLC, mobile phase 90:10 of 20 mM pH 4 KH$_2$PO$_4$:CH$_3$CN). A $^1$H-NMR (CDCl$_3$) spectrum of the sample showed the presence of 4-(3-bromo-1-ethyl-6-fluoro-4-oxo-1,4-dihydroquinolin-7-yl)-piperazine-1-carboxylic acid ethyl ester in >98% and 4-(3-bromo-1-ethyl-6-fluoro-4-oxo-1,4-dihydroquinolin-5-yl)-piperazine-1-carboxylic acid ethyl ester in <2%.

The filtrate was concentrated in vacuo and flash chromatography on silica gel using a mixture of solvent gradient (6:4:2 and 7:3:2 ethyl acetate:hexane:dichloromethane) afforded 5.3 g (15.6%) of 4-(3-bromo-1-ethyl-6-fluoro-4-oxo-1,4-dihydroquinolin-5-yl)-piperazine-1-carboxylic acid ethyl ester as a yellow solid and 4.2 g of 4-(3-bromo-1-ethyl-6-fluoro-4-oxo-1,4-dihydroquinolin-7-yl)-piperazine-1-carboxylic acid ethyl ester.

The total isolated yield of 4-(3-bromo-1-ethyl-6-fluoro-4-oxo-1,4-dihydroquinolin-7-yl)-piperazine-1-carboxylic acid ethyl ester and 4-(3-bromo-1-ethyl-6-fluoro-4-oxo-1,4-dihydroquinolin-7-yl)-piperazine-1-carboxylic acid ethyl ester from the last two paragraphs is 96.5% yield (% yield=(24.5 g*0.95+5.3 g+4.2 g) /425/0.0799*100%).

This experiment afforded 24.5 g of a 98:2 mixture of 4-(3-bromo-1-ethyl-6-fluoro-4- oxo-1,4-dihydroquinolin-7-yl)-piperazine-1-carboxylic acid ethyl ester to 4-(3-bromo-1-ethyl-6-fluoro-4-oxo-1,4-dihydroquinolin-7-yl)-piperazine-1-carboxylic acid ethyl ester (95% pure by Rp-HPLC), and 4.2 g of the desired compound 4-(3-bromo-1-ethyl-6-fluoro-4-oxo-1,4-dihydroquinolin-7-yl)-piperazine-1-carboxylic acid ethyl ester.

(ii) from 4-(1-Ethyl-6-fluoro-4-oxo-1,2,3,4-tetrahydroquinolin-7-yl)-piperazine-1-carboxylic acid ethyl ester (example 10)

To a solution of the compound from example 10 (173 mg, 0.5 mmol) in glacial acetic acid (2 ml) at room temperature was added a solution of bromine (192 mg, 1.2 mmol) in acetic acid (1 ml). The resulting mixture was stirred for 2 hours. Volatile materials were removed in vacuo and the residue was taken up in dichloromethane. The organic layer was successively washed with a solution of saturated sodium bicarbonate, 10% sodium sulfite and brine, then dried (sodium sulfate), filtered and concentrated to a solid. Purification by flash chromatography on silica gel using ethyl acetate followed by a mixture of dichloromethane and methanol (7:3) afforded 192 mg (90%) of 4-(3-bromo-1-ethyl-6-fluoro-4-oxo-1,4-dihydroquinolin-7-yl)-piperazine-1-carboxylic acid ethyl ester.

4-(3-bromo-1-ethyl-6-fluoro-4-oxo-1,4-dihydroquinolin-7-yl)-piperazine-1-carboxylic acid ethyl ester $^1$H-NMR (CDCl$_3$) δ 7.85 (d, 1H, J=13.2 Hz, H$_5$); 7.80 (s, 1H, H$_2$); 6.61 (d, 1H, $^4$J$_{HF}$=6.9 Hz,, H$_8$); 4.16 (q, 2H, J=7.1 Hz, CO$_2$CH$_2$CH$_3$); 4.10 (q, 2H, J=7.2 Hz, NCH$_2$CH$_3$); 3.66–3.69 (m, 4H); 3.15–3.18 (m, 4H); 1.45 (t, 3H, J=7.2 Hz, NCH$_2$CH$_3$) and 1.27 (t, 3H, J=7.1 Hz, CO$_2$CH$_2$CH$_3$).

$^{13}$C-NMR (CDCl$_3$) δ 171.2 (C$_4$), 155.5 (CO$_2$Et), 152.8 (J$_{CF}$=247 Hz), 144.6 ($^2$J$_{CF}$=11 Hz), 142.0, 136.4, 120.6 ($^3$J$_{CF}$=7 Hz), 113.0 ($^2$J$_{CF}$=23 Hz), 104.8, 103.8, 61.7, 50.1, 48.6, 43.7, 14.8, 14.5.

IR (KBr) (cm$^{-1}$): 1627 and 1692

MP: 198–203° C.

HRMS ( m/e: C$_{18}$H$_{21}$BrFN$_3$O$_3$) calc: 425.07503, found: 425.07555

4-(3-bromo-1-ethyl-6-fluoro-4-oxo-1,4-dihydroquinolin-5-yl)-piperazine-1-carboxylic acid ethyl ester $^1$H-NMR (CDCl$_3$)*(s, 1H, H$_2$); 7.34 (dd, 1H, $^3$J$_{HF}$=11.2 Hz, $^3$J$_{HH}$=9.5 Hz, H$_7$); 7.03 (dd, 1H, $^4$J$_{HF}$=3.8 Hz, $^3$J$_{HH}$=9.4 Hz, H$_8$); 4.10–4.19 (m, 4H, 2 CH$_2$CH$_3$); 3.67–3.70 (m, 4H); 3.23 (m, 4H); 1.47 (t, 3H, J=7.2 Hz, NCH$_2$CH$_3$) and 1.27 (t, 3H, J=7.1 Hz, CO$_2$CH$_2$CH$_3$)

$^{13}$C-NMR (CDCl$_3$)*171.9, 155.9, 154.8 (J$_{CF}$=242 Hz), 141.1, 138.6, 138.2, 123.2, 120.9 (J$_{CF}$=25 Hz), 110.2 (J$_{CF}$=8 Hz), 106.9, 61.3, 51.74, 51.67, 49.1, 44.7, 14.8, 14.4.

IR (KBr) (cm$^{-1}$): 1615 and 1680.

MP: 159–161° C.

HRMS (m/e: C$_{18}$H$_{21}$BrFN$_3$O$_3$) calc. 425.0750, found: 425.0756.

Example 6

4-(3-Cyano-1-ethyl-6-fluoro-4-oxo-1,4-dihydroquinolin-7-yl)-piperazine-1-carboxylic acid ethyl ester (formula X)

A mixture of compounds from example 5 (12.1 g, 28.4 mmol), CuI (5.4 g, 28.4 mmol) and KCN (1.9 g, 29 mmol) in 60 ml of 1-methyl-2-pyrrolidinone (NMP) was heated at 200–205° C. for 16 hours. On cooling to room temperature, the reaction mixture was diluted with chloroform at which time a thick white precipitate formed. The mixture was filtered over celite and the organic filtrate was washed with water (2×), dried ($Na_2SO_4$), filtered and concentrated in vacuo. NMP was then removed by distillation under reduced pressure. The residue was stirred in a mixture of 1:1 dichloromethane and methanol (200 ml), heated for 2 hours, cooled to room temperature and diluted with ethyl acetate (300 ml). The white suspension was stirred for 16 h and filtration gave 7.2 g of 4-(3-cyano-1-ethyl-6-fluoro-4-oxo-1,4-dihydroquinolin-7-yl)-piperazine-1-carboxylic acid ethyl ester X as a white solid. The volume of the mother liquor was reduced to ca. 100 mL and a white solid separated. Filtration afforded a second crop of X (2.1 g). Total yield: 9.3 g (88%).

$^1$H-NMR ($CDCl_3$+2 drops TFA-d)*8.26 (s, 1H, $H_2$); 7.92 (d, 1H, $^3J_{HF}$=12.9, $H_5$); 6.93 (d, 1H, $^4J_{HF}$=6.8 Hz, $H_8$); 4.24–4.39 (m, 4H, 2 $CH_2CH_3$); 3.75–3.78 (m, 4H); 3.37–3.40 (m, 4H); 1.60 (t, 3H, J=7.2 Hz, $NCH_2CH_3$) and 1.33 (t, 3H, J=7.2 Hz, $CO_2CH_2CH_3$)

$^{13}$C-NMR ($CDCl_3$+2 drops TFA-d)*174.4, 156.8, 153.8 ($J_{CF}$=251 Hz), 148.5, 146.3 ($J_{CF}$=10 Hz), 137.3, 120.3 ($J_{CF}$=8 Hz), 114.4, 113.1 ($J_{CF}$=24 Hz), 104.6, 94.4, 63.4, 50.5, 49.5, 43.7, 14.5, 14.3.

IR (KBr) ($cm^{-1}$): 1629, 1689 and 2222.

MP: 258–262° C.

HRMS (m/e: $C_{19}H_{21}FN_4O_3$) calc. 372.1598, found 372.1581.

Example 7

4-(3-Cyano-1-ethyl-6-fluoro-4-oxo-1,4-dihydroquinolin-5-yl)-piperazine-1-carboxylic acid ethyl ester (formula X)

A mixture of compounds from example 5 (4.8 g, 11.2 mmol), CuI (2.13 g, 11.2 mmol) and KCN (0.78 g, 12 mmol) in 25 mll of 1-methyl-2-pyrrolidinone (NMP) was heated at 200–205° C. for 16 hours. On cooling to room temperature, the reaction mixture was diluted with chloroform, filtered over celite and the organic filtrate was washed with water (2×), dried ($Na_2SO_4$), filtered and concentrated under vacuum. NMP was then removed by distillation under reduced pressure. The residue was purified by column chromatography on silica gel using a solvent mixture of 6:4:2 ethyl acetate, hexane and dichloromethane thereby affording 3.7 g (88%) of 4-(3-cyano-1-ethyl-6-fluoro-4-oxo-1,4-dihydroquinolin-5-yl)-piperazine-1-carboxylic acid ethyl ester as a yellow solid.

$^1$H-NMR ($CDCl_3$)*8.02 (s, 1H, $H_2$); 7.37 (dd,1H, $^3J_{HF}$=11.3 Hz, $^3J_{HH}$=9.4 Hz, $H_7$); 7.08 (dd, 1H, $^4J_{HF}$=3.7 Hz, $^3J_{HH}$=9.3 Hz, $H_8$); 4.11–4.21 (m, 4H, 2 $CH_2CH_3$); 3.60–3.63 (m, 4H); 3.18 (m, 4H); 1.49 (t, 3H, J=7.2 Hz, $NCH_2CH_3$) and 1.23 (t, 3H, J=7.1 Hz, $CO_2CH_2CH_3$)

$^{13}$C-NMR ($CDCl_3$)*174.0, 155.7, 155.3 ($J_{CF}$=244 Hz), 146.9, 138.9 ($J_{CF}$=10 Hz), 137.9, 123.4, 121.4 ($J_{CF}$=25 Hz), 116.2, 110.7 ($J_{CF}$=8 Hz), 96.5, 61.3, 51.7, 51.6, 50.0, 44.5, 14.7, 14.3.

IR (KBr) ($cm^{-1}$): 1635, 1689 and 2220.

MP: 203–206° C.

HRMS (m/e: $C_{19}H_{21}FN_4O_3$) calc. 372.1598, found 372.1577.

Example 8

1-Ethyl-6-fluoro-4-oxo-7-piperazin-1-yl-1,4-dihydroquinoline-3-carboxylic acid (Norfloxacin)

A suspension of 4-(3-cyano-1-ethyl-6-fluoro-4-oxo-1,4-dihydroquinolin-7-yl)-piperazine-1-carboxylic acid ethyl ester (4.5 g, 12.1 mmol) and 10 g (250 mmol) of sodium hydroxide in 25 ml and 25 ml of ethanol was heated at 110° C. for 16 hours. After ca. 1 hour of heating, a homogeneous yellow solution resulted. The progress of the reaction is monitored by TLC using a solvent mixture of 8:8:3 $CH_2Cl_2$:MeOH:$NH_3$.

On cooling to ca. 70° C., activated charcoal (1 g) and celite (ca. 5 g) were added, then the reaction mixture was filtered over celite and washed with cold water. The mixture was acidified with 3N HCl to pH 7.5 to give a voluminous white suspension. (At pH ca. 9, a white precipitate started forming). The mixture was kept at 0° C. for 16 hours.

The mixture was filtered and the solid was washed with water (2×), MeOH (1×) and ether (2×). After drying, 3.2 g (83%) of 1-ethyl-6-fluoro-4-oxo-7-piperazin-1-yl-1,4-dihydroquinoline-3-carboxylic acid was obtained as a white solid.

$^1$H-NMR (TFA-d)*9.27 (s, 1H, $H_2$); 8.28 (d, 1H, $^3J_{HF}$=12.3, $H_5$); 7.45 (d, 1H, $^4J_{HF}$=6.5 Hz, $H_8$); 4.83 (q, 2H, J=7.1 Hz, $CH_2CH_3$); 3.75–3.94 (m, 4H); and 1.73 (t, 3H, J=7.0 Hz, $NCH_2CH_3$)

$^{13}$C-NMR (TFA-d)*172.6, 171.7, 157.2 ($J_{CF}$=257 Hz), 150.4, 150.1 ($J_{CF}$=10 Hz), 141.1, 118.2 ($J_{CF}$=10 Hz), 114.0 ($J_{CF}$=25 Hz), 106.9, 105.8, 54.8, 48.2, 46.5, 14.3.

IR (KBr) ($cm^{-1}$): 1617, 1732 and 3433.

MP: 210–216° C.

HRMS (m/e: $C_{16}H_{18}FN_3O_3$) calc. 319.1332, found 319.1327.

Example 9

1-Ethyl-6-fluoro-4-oxo-5-piperazin-1-yl-1,4-dihydroquinoline-3-carboxylic acid

A suspension of 4-(3-cyano-1-ethyl-6-fluoro-4-oxo-1,4-dihydroquinolin-5-yl)-piperazine-1-carboxylic acid ethyl ester (372 mg, 1 mmol) and 1.5g (37.5 mmol) of sodium hydroxide in 10 ml and 10 ml of ethanol was heated at 110° C. for 16 h. On cooling to room temperature, the reaction mixture was acidified with 3N HCl to pH 7.35 then evaporated to dryness.

The residue was triturated with a 1:1 mixture of dichloromethane and ethanol (50 ml) and filtered to remove solid inorganic materials. The filtrate was then concentrated in vacuo. This procedure was repeated two more times.

The filtrate was concentrated then dissolved in 2 ml of a mixture of 1:1 dichloromethane and ethanol and diluted with 100 ml of hexane. The light yellow solid (290 mg, 91%), 1ethyl-6-fluoro-4-oxo-5-piperazin-1-yl-1,4-dihydroquinoline-3-carboxylic acid was collected by suction filtration.

$^1$H-NMR ($CDCl_3$/MeOD, 1:1, 1 drop TFA-D)*8.52 (s, 1H, $H_2$); 7.29–7.40 (m, 2H); 4.18 (q, 2H, J=7.2Hz, $CH_2CH_3$); 3.13–3.25 (m, 8H) and 1.26 (t, 3H, J=7.2 Hz, $NCH_2CH_3$)

$^{13}$C-NMR ($CDCl_3$/MeOD, 1:1, 1 drop TFA-d)*178.5, 168.1, 155.9 ($J_{CF}$=246 Hz), 147.5, 138.1, 136.9 ($J_{CF}$=11 Hz), 123.5, 122.7 ($J_{CF}$25 Hz), 113.9 ($J_{CF}$=9 Hz), 108.2, 50.4, 48.6, 48.5, 43.8, 13.7.

IR (KBr) ($cm^{-1}$): 1590–1625 and 2480–3423.

HRMS (m/e: $C_{16}H_{18}FN_3O_3$) calc. 319.1332, found 319.1333

Example 10

4-(1-Ethyl-6-fluoro-4-oxo-1,2,3,4-tetrahydroquinolin-7-yl)-piperazine-1-carboxylic acid ethyl ester A mixture of 1-ethyl-6,7-difluoro-1,2,3,4-tetrahydroquinolin-4-one (example 3) (105 mg, 0.5 mmol) in neat ethyl 1-piperazine carboxylate (790 g, 5.0 mol) was heated at 130–135° C. for 16 hours. After cooling to room temperature, the reaction mixture was diluted with dichloromethane and the organic layer was washed with sat. NH$_4$Cl solution, then with water, dried (Na$_2$SO$_4$), filtered and concentrated in vacuo to give a brown solid.

Purification by flash chromatography using a gradient of solvent mixture of hexane and ethyl acetate (8:2 and 1:1 mixture) afforded 173 mg (99%) of 4-(1-Ethyl-6-fluoro-4-oxo-1,2,3,4-tetrahydroquinolin-7-yl)-piperazine-1-carboxylic acid ethyl ester as a yellow solid.

$^1$H-NMR (CDCl$_3$) d (ppm): 7.48 (d, 1H, $^3$J$_{HF}$=13.4 Hz, H$_5$); 6.03 (d, 1H, $^4$J$_{HF}$=6.9 Hz, H$_8$); 4.13 (q, 2H, J=7.1 Hz, OCH$_2$CH$_3$); 3.58–3.59 (m, 4H), 3.37–3.39 (m, 4H), 3.09–3.10 (m, 4H), 2.57 (t, 2H), 1.25 (t, 3H, J=7.2 Hz, NCH$_2$CH$_3$), and 1.14 (t, 3H, J=7.1 Hz)

Example 11

3-[N-(3',4'-Difuorophenyl)-N'-cyclopropylamino] propionic acid (formula IV)

3-(3',4'-Difuorophenylamino)propionic acid (130 g, 0.65 mol) was dissolved in methanol (1 l) and was cooled to 0° C. Acetic acid (370 ml, 6.5 mol) was added and the solution was maintained below 100° C. while [(1-ethoxycyclopropyl)oxy]trimethylsilane (225 g, 1.3 mol) was added dropwise over period of 20 min, followed by NaCNBH$_4$ (90 g, 1.43 mol) over period of 20 min. After the addition was complete the reaction mixture was heated to gentle refluxing for 5 hours and then concentrated by reduced press distillation. With ice-bath cooling, water was added dropwise to the residue under a vigrous stirring, forming a suspension. The product was collected by filtration, rinsed with haxane, and dried in vaccum oven to give 134 g (yield 85.5%) of 3-[N-(3',4'-difuorophenyl)-N'-cyclopropylamino]propionic acid as a white solid.

$^1$H nmr (CDCl$_3$) δ 11.44 (br s, 1H, COOH), 7.02 (dd, 1H, J=9.3, 9.8 Hz, phenyl H), 6.83 (ddd, 1H, J=2.8, 6.8, 9.7 Hz, phenyl H), 6.63–6.66 (m, 1H, phenyl H). 3.72 (t, 2H, J=7.3 Hz, CH$_2$), 2.61 (q, 2H, J=7.3 Hz, CH$_2$), 2.36–2.42 (m, 1H, cyclopropyl H), 0.85–0.91 (m, 2H, cyclopropyl H), 0.59–0.64 (m, 2H, cyclopropyl H)

$^{13}$C nmr (CDCl$_3$) δ 179.0, 150.8 (J$_{CF}$=13, 243 Hz), 145.9 (J$_{CF}$=8 Hz), 143.7 (J$_{CF}$=1.3, 237 Hz), 117.2 (J$_{CF}$=17 Hz), 110.1, 104.0 (J$_{CF}$=21 Hz), 47.3, 31.6, 31.3, 9.3

IR (KBr) cm$^{-1}$: 1697 (C=O).

MP 81–83° C.

HRMS (m/e: C$_{12}$H$_{13}$F$_2$NO$_2$) calc. 241.0914, found 2.0907.

Example 12

1-Cyclopropyl-6,7-difluoro-1,2,3,4-tetrahydro-4-oxo-quinoline and 1-Cyclopropyl-5,6-difluoro-1,2,3, 4-tetrahydro-4-oxo-quinoline (formula VI)

3-[N-(3',4'-Difuorophenyl)-N'-cyclopropylamino] propionic acid (80 g, 0.33 mol) was mixed with Eaton's reagent (800 g) and the mixture was heated to 80° C. The mixture was stirred at that temperature for 3 hours and then carefully poured to 2.5 l cold water. The mixture was stirred for 30 min with ice-bath cooling to form a suspension. The product was collected by filtration, washed with cold water and dried in vaccum oven to give 64 g (yield 86%) of a 3:2 mixture of 1-cyclopropyl-6,7-difluoro-1,2,3,4-tetrahydro-4-oxo-quinoline and 1-cyclopropyl-5,6-difluoro-1,2,3,4-tetrahydro-4-oxo-quinoline as a yellow solid which is used directly for the subsequent reaction.

A small amount of the product mixture was purified by column chromatography (1% MeOH/CH$_2$Cl$_2$) to give the two regioisomers respectively.

1-Cyclopropyl-6,7-difluoro-1,2,3,4-tetrahydro-4-oxo-quinoline, yellow green solid $^1$H nmr (CDCl$_3$) δ 7.64 (dd, 1H, J=9.4, 10.3 Hz, phenyl H), 7.05 (dd, 1H, J=6.5, 13 Hz, phenyl H), 3.51 (t, 2H, J=7.1 Hz, CH$_2$), 2.62 (t, 2H, J=7.1 Hz, CH$_2$), 2.29–2.35 (m,1H, cyclopropyl H), 0.89–0.95 (m,1H, cyclopropyl H), 0.69–0.74 (m,1H, cyclopropyl H).

$^{13}$C nmr (CDCl$_3$) δ 191.8, 155.3 (J$_{CF}$=14, 253 Hz), 151.2(J$_{CF}$=10 Hz), 144.1 (J$_{CF}$=14, 240 Hz), 116.4, 115.8 (J$_{CF}$=3, 18 Hz), 103.2 (J$_{CF}$=22 Hz), 49.9, 38.5, 32.6, 8.6.

IR (KBr) cm$^{-1}$ 1674 (C=O).

MP 83–84° C.

HRMS (m/e: C$_{12}$H$_{11}$F$_2$NO)calc. 223.0809, found 223.0817.

1-Cyclopropyl-5,6-difluoro-1,2,3,4-tetrahydro-4-oxo-quinoline, yellow green solid $^1$H nmr (CDCl$_3$) δ 7.16–7.26 (m, 1H, phenyl H), 7.02 (ddd, 1H, J=2.0, 3.8, 9.4 Hz, phenyl H), 3.51 (t, 2H, J=7.1 Hz, CH$_2$), 2.64 (t, 2H, J=7.1 Hz, CH$_2$), 2.30–2.37 (m, 1H, cyclopropyl H), 0.90–0.96 (m, 1H, cyclopropyl H), 0.69–0.74 (m, 1H, cyclopropyl H).

$^{13}$C nmr (CDCl$_3$) δ 191.7, 150.2 (J$_{CF}$=13, 263 Hz), 150.3, 143.6 (J$_{CF}$=13, 238 Hz), 122.9 (J$_{CF}$=3, 18 Hz), 110.9, 109.4 (J$_{CF}$=5 Hz), 49.6, 40.1, 32.8, 8.9.

IR (KBr) cm$^{-1}$ 1673 (C=O).

MP 103–106° C.

HRMS C$_{12}$H$_{11}$F$_2$NO calc. 223.0809, found 223.0819.

Example 13

1-Cyclopropyl-3-bromo-6,7-difluoro-1,4-dihydro-4-oxo-quinoline and 1-Cyclopropyl-3-bromo-5,6-difluoro-1,4-dihydro-4-oxo-quinoline (formula VII)

A 3:2 mixture product of example 12 (21 g, 0.095 mol) was dissolved in acetic acid (100 ml) and heated to 60° C. Bromine (52 g, 0.33 mol) in acetic acid (50 ml) was added dropwise over period of 3 hr while the temperature was maintained at 60° C. After the addition was completed the mixture was stirred for further 10 min and 300 ml water was added carefully. The resulting yellow suspension was cooled with ice-bath and filtered. The solid was washed with cold water, small amount 50% EtOH and ether, and dried in vacuum oven to give 51.6 g (yield 83%) of product as a 3:2 mixture of 1-cyclopropyl-3-bromo-6,7-difluoro-1,4-dihydro-4-oxo-quinoline and 1-cyclopropyl-3-bromo-5,6-difluoro- 1,4-dihydro-4-oxo-quinoline, which is used directly for the subsequent reaction.

A small amount of 1-cyclopropyl-3-bromo-6,7-difluoro-1,4-dihydro-4-oxo-quinoline 5 was isolated from the mixture by column chromatography (3:7 EtOAc/hexane) as a white solid $^1$H nmr (CDCl$_3$) δ 8.08 (dd, 1H, J=8.8, 10.4 Hz, phenyl H), 8.05 (s, 1H, vinyl H), 7.69 (dd,1H, J=6.5, 11.5 Hz, phenyl H), 3.41–3.48 (m,1H, cyclopropyl H), 1.31–1.41 (m, 2H, cyclopropyl H), 1.12–1.17 (m, 2H, cyclopropyl H).

$^{13}$C nmr (CDCl$_3$) δ 171.2, 153.5 (J$_{CF}$=254 Hz), 148.5 (J$_{CF}$=249 Hz), 143.2, 138.0 (J$_{CF}$=10 Hz), 122.0, 114.7 (J$_{CF}$=19 Hz), 105.3 (J$_{CF}$=23 Hz), 105.1, 34.6, 8.5.

IR (KBr) cm$^{-1}$ 1611 (C=O).

MP 214–216° C.

HRMS (m/e: $C_{11}H_8BrF_2NO$) calc. 298.9757, found 298.9755.

A small amount of 1-cyclopropyl-3-bromo-5,6-difluoro-1,4-dihydro-4-oxo-quinoline was isolated by preparative TLC (5:65:30 $CH_2Cl_2$/EtOAc/hexane) as a white solid $^1$H nmr (CDCl$_3$) δ 8.45 (s, 1H, vinyl H), 7.89–7.94 (m, 2H, phenyl H), 3.54–3.61 (m, 1H, cyclopropyl H), 1.08–1.24 (m, 4H, cyclopropyl H).

$^{13}$C nmr (CDCl$_3$) δ 143.6, 138.6,, 121.3 ($J_{CF}$=19 Hz), 115.6, 113.8, 104.6, 34.9, 8.0.

IR (KBr) cm$^{-1}$ 1627 (C=O).

MP 264–265° C.

HRMS (m/e: $C_{11}H_8BrF_2NO$) calc. 298.9757, found 298.9752.

Example 14

4-(3-Bromo-1-cyclopropyl-6-fluoro-4-oxo-1,4-dihydroquinolin-7-yl)-piperazine-1-carboxylic acid ethyl ester and 4-(3-Bromo-1-cyclopropyl-6-fluoro-4-oxo-1,4-dihydroquinolin-5-yl)-piperazine-1-carboxylic acid ethyl ester (formula IX)

A (1:1) mixture of 3-bromo-1-cyclopropyl-6,7-difluoro-1H-quinolin-4-one and 3-bromo-1-cyclopropyl-5,6-difluoro-1H-quinolin-4-one (22.5 g, 0.075 mol) in neat ethyl piperazine carboxylate (118.5 g, 0.75 mol) was heated at 110–115° C. for 14 h. After cooling to room temperature, the reaction mixture was diluted with ethyl acetate (300 mL) and hexane (50 mL). The solid suspension was stirred while cooling to room temperature. After cooling in ice for 30 min, the solid was collected by suction filtration. The solid was dissolved in chloroform, and the organic layer was successively washed with a saturated ammonium chloride solution and brine, dried (Na$_2$SO$_4$), filtered and concentrated in vacuo. The off-white solid was suspended in hot ethyl acetate, then collected by suction filtration to afford 15.5 g (45%) of the desired product 4-(3-bromo-1-cyclopropyl-6-fluoro-4-oxo-1,4-dihydroquinolin-7-yl)-piperazine-1-carboxylic acid ethyl ester as a white solid.

The filtrate was concentrated in vacuo, then diluted with hexane (500 mL) with vigorous stirring as a sticky solid deposited on the side of the flask. The supernatant solution was decanted and the pasty brown residue was taken up in chloroform. The organic layer was washed with a saturated solution of ammonium chloride, brine, dried (Na$_2$SO$_4$). Activated charcoal and celite were then added and the mixture was filtered over celite. Concentration gave a yellow solid which was then suspended in cold ethyl acetate and suction filtration afforded 12.9 g (39%) of 4-(3-bromo-1-cyclopropyl-6-fluoro-4-oxo-1,4-dihydroquinolin-5-yl)-piperazine-1-carboxylic acid ethyl ester as a yellow solid.

4-(3-Bromo-1-cyclopropyl-6-fluoro-4-oxo-1,4-dihydroquinolin-7-yl)-piperazine-1-carboxylic acid ethyl ester $^1$H-NMR (CDCl$_3$)*7.92 (s, 1H, H$_2$); 7.78 (d,1H, $^3J_{HF}$=13.2 Hz, H$_5$); 7.16 (d, 1H, $^4J_{HF}$=7.1 Hz,, H$_8$); 4.18 (q, 2H, J=7.0 Hz, CO$_2$CH$_2$CH$_3$); 3.70 (m, 4H); 3.40–3.41 (m, 1H, NCHCH$_2$); 3.20–3.22 (m, 4H); 1.29 (t, 3H, J=7.0 Hz, COCH$_2$CH$_3$); 1.27–1.31 (m, 2H, NCHCH$_2$) and 1.10 (br., 2H, NCHCH$_2$)

$^{13}$C-NMR (CDCl$_3$)*171.2, 155.6, 153.0 ($J_{CF}$=247 Hz), 144.4 ($J_{CF}$=11 Hz), 142.3, 138.4, 119.9, 112.6 ($J_{CF}$=23 Hz), 104.8, 104.5, 61.8, 50.0, 43.7, 34.3, 14.8, 8.4.

IR (KBr) (cm$^{-1}$): 1629 and 1720.

MP: 260–262° C.

HRMS (m/e: $C_{19}H_{21}BrFN_3O_3$) calc: 437.0750, found: 437.0748

4-(3-Bromo-1-cyclopropyl-6-fluoro-4-oxo-1,4-dihydroquinolin-5-yl)-piperazine-1-carboxylic acid ethyl ester $^1$H-NMR (CDCl$_3$)*7.96 (s, 1H, H$_2$); 7.52 (dd, 1H, $^4J_{HF}$=4.1 Hz, $J_{HH}$=9.4 Hz, H$_7$); 7.28–7.35 (dd, 1H, $^3J_{HF}$=11.2 Hz, $J_{HH}$=9.5 Hz, H$_8$); 4.12 (q, 2H, J=7.1 Hz, CO$_2$CH$_2$CH$_3$); 3.63–3.66 (m, 4H); 3.31–3.38 (m, 1H, NCHCH$_2$); 3.18 (m, 4H); 1.24 (t, 3H, J=7.1 Hz, COCH$_2$CH$_3$); 1.21–1.30 (m, 2H, NCHCH$_2$) and 0.90–1.04 (m, 2H, NCHCH$_2$)

$^{13}$C-NMR (CDCl$_3$)*171.8, 155.8, 155.0 ($J_{CF}$=242 Hz), 141.1, 140.1, 138.2 ($J_{CF}$=10 Hz), 122.3, 120.7 ($J_{CF}$=25 Hz), 111.4 ($J_{CF}$=8 Hz), 106.4, 61.2, 51.7, 51.6, 34.8, 14.8, 8.9.

IR (KBr) (cm$^{-1}$): 1621 and 1691.

MP: 180–183° C.

HRMS (m/e: $C_{19}H_{21}BrFN_3O_3$), calc: 437.0750, found: 437.0756.

Example 15

4-(3Cyano-1-cyclopropyl-6-fluoro-4-oxo-1,4-dihydroquinolin-7-yl)-piperazine-1-carboxylic acid ethyl ester (X)

A mixture of 4-(3-bromo-1-cyclopropyl-6-fluoro-4-oxo-1,4-dihydroquinolin-7-yl)-piperazine-1-carboxylic acid ethyl ester (11.0 g, 25.1 mmol), CuI (5.3 g, 27.6 mmol) and KCN (1.8 g, 27.6 mmol) in 110 mL of 1-methyl-2-pyrrolidinone (NMP) was heated at 200–205° C. for 16 hours. On cooling to room temperature, the reaction mixture was diluted with chloroform (250 ml) upon which a thick precipitate formed. The mixture was filtered over celite (2×) and the clear brown organic filtrate was washed with water/brine (2×), dried (Na$_2$SO$_4$), filtered and concentrated in vacuo to a black oil. An off-white solid precipitated out by addition of hexane (150 ml) and ethyl acetate (300 ml). The solid was dissolved in chloroform, and activated charcoal and celite were added. The mixture was then filtered over celite. Evaporation of the solvent gave a white solid which was suspended in hot ethyl acetate and filtration afforded 9.1 g (94%) of 4-(3-cyano-1-cyclopropyl-6-fluoro-4-oxo-1,4-dihydroquinolin- 7-yl)-piperazine-1-carboxylic acid ethyl ester as a white solid.

$^1$H-NMR (CDCl$_3$+3 drops of TFA-d)*8.24 (s, 1H, H$_2$); 7.75 (d, 1H, $^3J_{HF}$=13.0 Hz, H$_5$); 7.38 (d, 1H, $^4J_{HF}$=7.0 Hz, H$_8$); 4.23 (q, 2H, J=7.0 Hz, CO$_2$CH$_2$CH$_3$); 3.76 (m, 4H), 3.61–3.63 (m,1H, NCHCH$_2$); 3.37–3.38 (m, 4H); 1.42–1.44 (m, 2H, NCHCH$_2$); 1.32 (t, 3H, J=7.1 Hz, COCH$_2$CH$_3$) and 1.20–1.21 (br., 2H, NCHCH$_2$)

$^{13}$C-NMR (CDCl$_3$+3 drops of TFA-d)*174.4, 156.6, 153.8 ($J_{CF}$=251 Hz), 148.8, 145.9 ($J_{CF}$=10 Hz), 139.0, 119.6, 114.6, 112.4 ($J_{CF}$=24 Hz), 105.5, 94.4, 63.1, 49.4, 43.6, 36.0, 14.5, 8.3.

IR (KBr) (cm$^{-1}$) 1627, 1709 and 2222.

HRMS (m/e: $C_{20}H_{21}FN_4O_3$) calc: 384.1598, found: 384.1602.

Example 15A 4-(3-Cyano-1-cyclopropyl-6-fluoro-4-oxo-1,4-dihydroquinolin-5-yl)-piperazine-1-carboxylic acid ethyl ester (formula X)

A mixture of 4-(3-bromo-1-cyclopropyl-6-fluoro-4-oxo-1,4-dihydroquinolin-5-yl)-piperazine-1-carboxylic acid ethyl ester (8.0 g, 18.3 mmol), CuI (3.81 g, 20.0 mmol) and KCN (1.3 g, 20 mmol) in 50 ml of 1-methyl-2-pyrrolidinone (NMP) was heated at 200–205° C. for 16 hours. On cooling to room temperature, the reaction mixture was diluted with chloroform, filtered over celite and the organic filtrate was washed with water/brine (2×), dried ($Na_2SO_4$), filtered and concentrated in vacuo. NMP was then removed by distillation under reduced pressure. The residue was suspended in hot ethyl acetate, then filtered by suction filtration to afford 6.9 g of crud product. Recrystallization from dichloromethane and ethyl acetate afforded 6.4 g (92%) of 4-(3-cyano-1-cyclopropyl-6-fluoro-4-oxo-1,4-dihydroquinolin-5-yl)-piperazine-1-carboxylic acid ethyl ester as a yellow solid. The compound was suspended in 1:1 mixture of $EtOH/CH_2CH_2$ and 10%Hcl in isopropanol was added with stirring. The resulting mixture was cooled with ice bath for 2 hr and filtered to afford ciprofloxacin hydrochloride salt as a white solid.

$^1$H-NMR ($CDCl_3$)*8.07 (s, 1H, $H_2$); 7.58 (dd, 1H, $^4J_{HF}$=4.0 Hz, $J_{HH}$=9.3 Hz, $H_8$); 7.39 (dd, 1H, $^3J_{HF}$=11.4 Hz, $J_{HH}$=9.4 Hz, $H_7$); 4.14 (q, 2H, J=7.1 Hz, $CO_2CH_2CH_3$); 3.64 (m, 4H); 3.39–3.46 (m, 1H, $NCHCH_2$); 3.18 (m, 4H); 1.31–1.37 (m, 2H, $NCHCH_2$); 1.26 (t, 3H, J=7.1 Hz, $COCH_2CH_3$) and 1.07–1.13 (m, 2H, $NCHCH_2$)

$^{13}$C-NMR ($CDCl_3$)*173.8, 155.8, 155.6 ($J_{CF}$=244 Hz), 147.1, 139.9, 138.7 ($J_{CF}$=10 Hz), 122.7, 121.3 ($J_{CF}$=25 Hz), 116.0, 111.6 ($J_{CF}$=8 Hz), 96.7, 61.4, 51.8, 51.7, 44.6, 35.7, 14.8, 8.7.

IR (KBr) ($cm^{-1}$): 1631, 1709 and 2222.

HRMS (m/e: $C_{20}H_{21}FN_4O_3$) calc. 384.1598, found: 384.1591.

Example 16

1-Cyclopropyl-6-fluoro-4-oxo-7-piperazin-1-yl-1,4-dihydroquinoline-3-carboxylic acid monohydrochloride (Ciprofloxacin hydrochloride)

A suspension of 4-(3-cyano-1-cyclopropyl-6-fluoro-4-oxo-1,4-dihydroquinolin-7-yl)-piperazine-1-carboxylic acid ethyl ester (15.0 g, 39 mmol) and 31.2 g (0.78 mol) of sodium hydroxide in 75 ml and 75 ml of ethanol was heated at 110° C. for 16 hours.

Ethanol was distilled off and the mixture was diluted with water. Activated charcoal (1 g) and celite* (ca. 5 g) were added, then the mixture was filtered over celite*. The light yellow solution was acidified with 3N HCl to pH 7.15. At pH 8.5, a white precipitate started forming. The mixture was kept at 0° C. for 2 hours, then filtered by suction filtration and the solid was dried under vacuum at 50° C. for 16 hours.
* trade-mark.

The solid was suspended in ethanol and dichloromethane (150 ml each), and 90 ml of HCl in iso-propanol (9.6%) was added. The mixture was cooled in ice for 2 hours, then filtered. The solid was washed with water, ethyl acetate and ethanol, and dried under vacuum at 55° C. for 24 hours thereby affording 13.4 g (93%) of 1-cyclopropyl-6-fluoro-4-oxo-7-piperazin-1-yl-1,4-dihydroquinoline-3-carboxylic acid. The compound was suspended in 1:1 mixture of $EtOH/CH_2CH_2$ and 10%Hcl in isopropanol was added with stirring. The resulting mixture was cooled with ice bath for 2 hr and filtered to afford 1-cyclopropyl-6-fluoro-4-oxo-7-piperazin-1-yl-1,4-dihydroquinoline-3-carboxylic acid hydrochloride salt as a white solid.

$^1$H-NMR ($CDCl_3$)*9.28 (s, 1H, vinyl H); 8.24 (d, 1H, J=12.3 Hz, phenyl H); 7.92 (d, 1H, J=5.7 Hz, phenyl H); 4.09 (br s, 1H, NH); 3.99 (br s, 4H, $2CH_2$); 3.77 (br s, 4H, $2CH_2$); 1.65–1.66 (m, 2H); 1.41 (br s, 2H).

$^{13}$C-NMR ($CDCl_3$)*173.8, 172.8, 158.8 ($J_{CF}$=259 Hz), 152.0, 151.1 ($J_{CF}$=10 Hz), 144.1, 118.5 ($J_{CF}$=10 Hz), 114.7 ($J_{CF}$=25 Hz), 108.7, 106.3, 49.1, 47.3, 41.5, 10.5.

IR (KBr) ($cm^{-1}$): 3432 (OH), 1721 (C=O).

HRMS (m/e: $C_{17}H_{18}FN_3O_3$) calc. 331.1332, found 331.1325.

Example 17

1-Cyclopropyl-6-fluoro-4-oxo-5-piperazin-1-yl-1,4-dihydroquinoline-3-carboxylic acid hydrochloride (formula I)

A suspension of 4-(3-cyano-1-cyclopropyl-6-fluoro-4-oxo-1,4-dihydroquinolin-5-yl)-piperazine-1-carboxylic acid ethyl ester (5.1 g, 13.3 mmol) and 10.6 g (266 mmol) of sodium hydroxide in 25 mL and 25 mL of ethanol was heated at 110° C. for 16 hours. On cooling to room temperature, celite and activated charcoal were added. The mixture was filtered over celite and the clear yellow solution was acidified with 3N HCl to pH 7.15. The mixture was cooled in ice for 2 hours, then filtered. The solid was washed with water, ethyl acetate and ethanol, and dried under vacuum at 50° C. for 16 hours.

The yellow solid was dissolved in dichloromethane (20 ml) and iso-propanol (30 ml) and 10 ml of HCl in iso-propanol (9.6%) was added. Dichloromethane was removed by vacuum distillation and a yellow solid deposited. A further 80 ml of iso-propanol was added and the mixture was chilled in ice for 2 hours. The yellow solid was collected by suction filtration and dried under vacuum at 50° C. for 16 h thereby affording 4.2 g (86%), 1-cyclopropyl-6-fluoro-4-oxo-5-piperazin-1-yl-1,4-dihydroquinoline-3-carboxylic acid.

$^1$H-NMR ($CDCl_3$)*8.52 (s, 1H, vinyl H); 7.87 (dd, 1H, J=4.0, 9.6 Hz, phenyl H); 7.52 (dd, 1H, J=9.6, 12.0 Hz, phenyl H); 3.46–3.52 (m, 1H); 3.28 (m, 8H, $4CH_2$); 1.14–1.21 (m, 2H); 0.88–0.95 (m, 2H).

$^{13}$C-NMR ($CDCl_3$)*180.0, 171.1, 157.2 ($J_{CF}$=246 Hz), 149.2, 141.4, 137.2 ($J_{CF}$=12 Hz), 124.8 ($J_{CF}$=25 Hz), 122.6, 116.6 ($J_{CF}$=9 Hz), 108.2, 49.94, 49.85, 45.2, 38.2, 9.0.

IR (KBr) ($cm^{-1}$): 3500 (OH), 1709 (C=O).

HRMS (m/e: $C_{17}H_{18}FN_3O_3$) calc. 331.1332, found 331.1338.

What is claimed is:

1. A process for the manufacture of compounds of formula I:

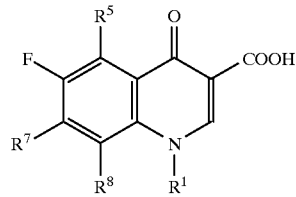

Formula I wherein $R^1$ is $C_1$–$C_8$ alkyl or cycloalkyl;

$R^8$ is hydrogen, $C_1$–$C_8$ alkyl, $C_1$–$C_8$ alkoxy or halogen; or R8 and $R^1$ taken together represent an ether group of the formula

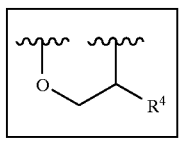

wherein

R⁴ is hydrogen or $C_1$–$C_8$ alkyl,

R⁵ is hydrogen,

R⁷ is NRR' wherein R and R' are independently hydrogen, $C_1$–$C_8$ alkyl, pyrrolidinyl, piperazinyl, prolyl, morpholinyl, piperidinyl; or is a group of formula:

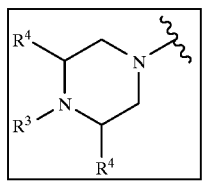

wherein

R4 is described as above;

R3 is hydrogen, alkyl, alkoxycarbonyl, benzyloxycarbonyl, alkanoyl; or is a group of formula:

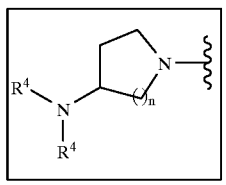

wherein

R⁴ is defined above;

n is 1 or 2 which comprises the following steps:

(a) brominating a compound of formula VI:

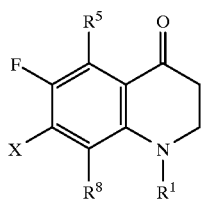

Formula VI wherein $R^1$, $R^5$ and $R^8$ are as defined above to give a compound of formula VII

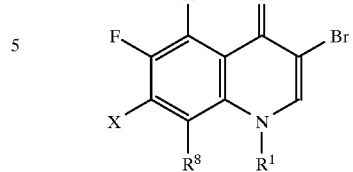

Formula VII wherein $R^1$, $R^5$, $R^8$ and X are as defined above;

(b) reacting a compound of formula VII with an amine of formula $R^7H$, to give a compound of formula IX

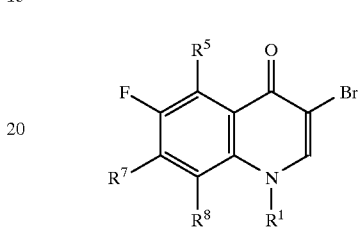

Formula IX wherein $R^1$, $R^5$, $R^7$ and $R^8$ are as defined above;

(c) reacting a compound of formula IX with KCN, CuI in the presence of 1-methyl-2-pyrrolidinone at a temperature between 190° C. and 210° C. to give a compound of formula X

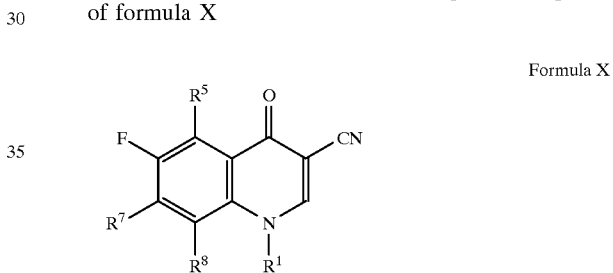

Formula X wherein $R^1$, $R^5$, $R^7$ and $R^8$ are as defined above; followed by:

(d) hydrolysing the compound of formula X in the presence of sodium hydroxide in a mixture of ethanol and water at 110° C. to give a compound of formula I.

2. The process of claim 1 wherein $R^1$ is ethyl, $R^5$ is hydrogen, $R^7$ is piperazinyl, $R^8$ is hydrogen and X is chloro.

3. The process of claim 1 wherein $R^1$ is cyclopropyl, $R^5$ is hydrogen, $R^7$ is piperazinyl, $R^8$ is hydrogen and X is chloro.

4. The process of claim 1 wherein at least 2.10 molar equivalents of bromine is used per mole of compound VI to carry out the bromination.

5. The process of claim 4 wherein the bromination is carried out in the presence of acetic acid at a temperature between 35° C. and 80° C.

6. The process of claim 1 wherein the amination is carried out at temperature between 110° C. and 130° C.

7. The process of claim 6 wherein the amination takes place in the presence of an inert solvent.

8. 1-ethyl-3-bromo-6,7-difluoro-1,4-dihydro-4-oxo-quinoline.

9. 1-cyclopropyl-3-bromo-6,7-difluoro-1,4-dihydro-4-oxo-quinoline.

10. 4-(3-bromo-1-ethyl-6-fluoro-4-oxo-1,4-dihydroquinolin-7-yl)-piperazine-1-carboxylic acid ethyl ester.

11. 4-(3-bromo-1-cyclopropyl-6-fluoro-4-oxo-1,4-dihydroquinolin-7-yl)-piperazine-1-carboxylic acid ethyl ester.

12. 4-(3-cyano-1-ethyl-6-fluoro-4-oxo-1,4-dihydroquinolin-7-yl)-piperazine-1-carboxylic acid ethyl ester.

13. 4-(3-cyano-1-cyclopropyl-6-fluoro-4-oxo-1,4-dihydroquinolin-7-yl)-piperazine-1-carboxylic acid ethyl ester.

14. The process of claim 1 wherein $R^1$ and $R^8$ taken together represent an ether radical group of the formula:

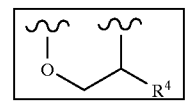

15. The process of claim 14 wherein $R^5$ is hydrogen, $R^4$ is methyl, and $R^7$ is 4-methyl-piperazinyl.

16. The process of claim 1 wherein $R^1$ is ethyl, $R^5$ is hydrogen, $R^8$ is fluoro and $R^7$ is 3-methyl-piperazinyl.

* * * * *